US008759091B2

(12) United States Patent
Tovey et al.

(10) Patent No.: US 8,759,091 B2
(45) Date of Patent: Jun. 24, 2014

(54) GENE REPORTER ASSAY, KIT AND CELLS WITH IMPROVED SENSITIVITY AND/OR SPECIFICITY FOR DETERMINING THE LEVEL OF AN EXTRACELLULAR SIGNAL

(75) Inventors: Michael G. Tovey, Paris (FR); Christophe Lallemand, Paris (FR)

(73) Assignees: Le Centre National de la Recherche Scientifique, Cedex, Paris (FR); Biomonitor Limited, Galway (IE)

( * ) Notice: Subject to any disclaimer, the term of this patent is extended or adjusted under 35 U.S.C. 154(b) by 1150 days.

(21) Appl. No.: 11/928,965

(22) Filed: Oct. 30, 2007

(65) Prior Publication Data
US 2008/0138818 A1    Jun. 12, 2008

Related U.S. Application Data

(60) Provisional application No. 60/863,479, filed on Oct. 30, 2006.

(51) Int. Cl.
*C12N 15/85* (2006.01)

(52) U.S. Cl.
USPC .......................................... 435/325

(58) Field of Classification Search
None
See application file for complete search history.

(56) References Cited

U.S. PATENT DOCUMENTS

| | | | |
|---|---|---|---|
| 5,401,629 A | 3/1995 | Harpold et al. | |
| 5,436,128 A | 7/1995 | Harpold et al. | |
| 5,707,803 A | 1/1998 | Lamb et al. | |
| 6,194,173 B1 * | 2/2001 | Czech et al. | 435/69.1 |
| 6,316,692 B1 | 11/2001 | Readhead et al. | |
| 6,673,897 B1 * | 1/2004 | Beyaert et al. | 530/350 |
| 7,045,281 B2 | 5/2006 | Livelli et al. | |
| 7,470,536 B2 | 12/2008 | Tovey et al. | |
| 2004/0235157 A1 | 11/2004 | Tovey et al. | |
| 2005/0042643 A1 * | 2/2005 | Cotter et al. | 435/6 |
| 2005/0196743 A1 * | 9/2005 | Ostanin et al. | 435/4 |
| 2007/0099245 A1 | 5/2007 | Gorovits et al. | |
| 2007/0124581 A1 * | 5/2007 | Khare et al. | 713/158 |
| 2008/0081327 A1 | 4/2008 | Livelli et al. | |
| 2008/0138818 A1 | 6/2008 | Tovey et al. | |
| 2008/0248516 A1 | 10/2008 | Livelli et al. | |
| 2009/0005330 A1 * | 1/2009 | Jimenez et al. | 514/44 |
| 2009/0111178 A1 | 4/2009 | Tovey et al. | |
| 2009/0136947 A1 | 5/2009 | Tovey et al. | |

FOREIGN PATENT DOCUMENTS

| | | | |
|---|---|---|---|
| JP | 2005253385 A * | 9/2005 | |
| WO | 2004027374 A2 | 4/2004 | |
| WO | 2004039990 A2 | 5/2004 | |
| WO | 2008055153 A2 | 5/2008 | |

OTHER PUBLICATIONS

Berghe et al., The Journal of Biological Chemistry, 1998, vol. 273, pp. 3285-3290.*
Gerstein et al., Genome Research, 2007, vol. 17, pp. 669-681.*
Manna et al., IFN-alpha suppresses activation of nuclear transcription factors NF-kappa B and activator protein 1 and potentiates TNF-induced apoptosis, Journal of Immunology, 165(9)4927-4934 (2000).
Darnay et al., Activation of NF-kB by RANK requires tumor necrosis factor receptor-associated factor (TRAF) 6 and NF-kB-inudcing kinase, The Journal of Biological Chemistry, 274(12):7724-7731 (1999).
Ganster et al., Complex regulation of human inducible nitric oxide synthase gene transcription by Stat 1 and NF-kB, PNAS, 98(15):8638-8643 (2001).
Hammerling et al., The beta-gal interferon assay: A new, precise, and sensitive method, Journal of Interferon and Cytokine Research, 18:451-460 (1998).
Office Action dated Apr. 7, 2006 of U.S. Appl. No. 10/677,777.
Office Action dated Sep. 7, 2007 of U.S. Appl. No. 10/677,777.
Office Action dated Mar. 19, 2008 of U.S. Appl. No. 10/677,777.
Office Action dated Oct. 16, 2009 of U.S. Appl. No. 11/765,262.
Office Action dated May 21, 2010 of U.S. Appl. No. 11/765,262.
Office Action dated Aug. 21, 2009 of U.S. Appl. No. 12/260,871.
Office Action dated Apr. 12, 2010 of U.S. Appl. No. 12/260,871.
Ausubel et al, Current protocols in molecular biology, 4:A.3F.5-10.
Canosi et al., A highly precise reporter gene bioassay for type I interferon, Journal of Immunological Methods, 199:69-76 (1996).
Files et al., A novel sensitive and selective bioassay for human type I interferons, Journal of Interferon and Cytokine Research, 18:1019-1024 (1998).
Lallemand et al., Constitutive expression of specific interferon isotypes in peripheral blood leukocytes from normal individuals and in promonocytic U937 cells, Journal of Leukocyte Biology, 60:137-146 (1996).
Lewis, A sensitive biological assay for interferons, Journal of Immunological Methods, 185:9-17 (1995).
Button et al., Aequorin-expressing mammalian cell lines used to report Ca2+ mobilization, Cell Calcium (Oct. 1993) 14(9):663-671.
Ahern H., Biochemical, reagents kits offer scientists good return on investment, The Scientist, 9(15):20-27 (1995).
ATCC catalog 1998.
Shen et al., The Journal of Biological Chemistry, 261(17):7762-7770.
Aschele et al., Cancer Research, 52:1855-1864 (1992).
Malucchi et al., Neurology, 62(11):2031-2037 (Jun. 2004).

(Continued)

*Primary Examiner* — Anne Gussow
*Assistant Examiner* — Mindy G Brown
(74) *Attorney, Agent, or Firm* — Browdy and Neimark, PLLC

(57) ABSTRACT

The present invention provides a reporter gene containing cell line with increased specificity and/or sensitivity for a particular extracellular signal of interest so that it can be used in a gene-reporter assay to accurately determine the presence and/or level of the extracellular signal of interest in the presence of other extracellular signals that are capable of activating the same signal transduction pathway as the extracellular signal of interest or that are capable of activating another signal transduction pathway capable of modulating the transcription of the reporter gene.

27 Claims, 5 Drawing Sheets

(56) References Cited

OTHER PUBLICATIONS

Deisenhammer F, Schellekens H, Bertolotto A., Measurement of neutralizing antibodies to interferon beta in patients with multiple sclerosis, J. Neurol. (2004) 251(Suppl. 2):II:31-II:39.

Lleonart et al., (1990) A novel, quantitative bioassay for type I interferon using a recombinant indicator cell line. Biotechnology 8:1263-1267.

Tovey et al., Characterization of neutralizing antibodies to interferons using a novel cell-based assay, Journal of Interferon and Cytokine Research, 27(8):735 (2007).

Farrell et al., Development and validation of luciferase reporter gene assay to measure anti-interferon beta neutralizing antibodies, Neurology, 68(12):(Suppl. 1):A117-A118 (2007).

Bertolotto et al., Interferon beta neutralizing antibodies in multiple sclerosis: neutralizing activity and cross-reactivity with three different preparations, Immunopharmacology, 48:95-100 (2000).

Nagy et al., Preparing feeder cell layers from STO or mouse embryo fibroblast (MEF) cells: Treatment with y-irradiation, Cold Spring Harb. Protoc.; 2006; doi:10.1101/pdb.prot4400.

Nagy et al., Preparing feeder cell layers from STO or mouse embryo fibroblast (MEF) cells: Treatment with mitomycin C, Cold Spring Harb. Protoc.; 2006; doi:10.1101/pdb.prot4399.

Yang et al., PNAS, 87:9568-9572 (1990).

Berry et al., Biochemical Pharmacology, 62:582-591 (2001).

Wei et al., Sheng Wu Hua Xue Yu Sheng Wu Wu Li Lue Bao, Shanghai, 33(1):123-127, abstract (2001).

Eichbaum et al., J. Exp. Med., 179:1985-1996 (1994).

Kim et al., Immunopharmacology and Immunotoxicology, 23(1):55-66 (2001).

Office Action dated Nov. 24, 2010 of U.S. Appl. No. 12/336,121.

Office Action dated Apr. 14, 2010 of U.S. Appl. No. 12/336,121.

\* cited by examiner

GENE REPORTER ASSAY, KIT AND CELLS WITH IMPROVED SENSITIVITY AND/OR SPECIFICITY FOR DETERMINING THE LEVEL OF AN EXTRACELLULAR SIGNAL

CROSS-REFERENCE TO RELATED APPLICATIONS

This application claims the benefit of priority from U.S. provisional application No. 60/863,479 filed Oct. 30, 2006, the entire content of which is incorporated herein by reference.

BACKGROUND OF THE INVENTION

1. Field of the Invention

The present invention relates to a gene reporter assay and a kit for determining the presence and/or the level in a sample of an extracellular signal that activates the signal transduction activity of a cell surface molecule or complex. The present invention further relates to a cell line which can be used in such an assay.

2. Description of the Related Art

Cell surface proteins permit intracellular transduction of extracellular signals. Cell surface proteins provide eukaryotic, as well as prokaryotic, cells a means to detect extracellular signals and transduce such signals intracellularly in a manner that ultimately results in a cellular response or a concerted tissue or organ response. Cell surface proteins, by intracellularly transmitting information regarding the extracellular environment via specific intracellular pathways induce an appropriate response to a particular stimulus. The response may be immediate and transient, slow and sustained, or some mixture thereof. By virtue of an array of varied membrane surface proteins, eukaryotic cells are exquisitely sensitive to their environment.

Extracellular signal molecules, such as cytokines, growth factors, hormones, vasodilators and neurotransmitters, exert their effects, at least in part, via interaction with cell surface proteins. For example, some extracellular signal molecules cause changes in transcription of target gene via changes in the levels of secondary messengers, such as cAMP. Other signals indirectly alter gene expression by activating the expression of genes, such as immediate-early genes that encode regulatory proteins, which in turn activate expression of other genes that encode transcriptional regulatory proteins. Other extracellular signal molecules cause activation of latent cytoplasmic signal transducers and activators of transcription (STAT) protein that enhance the transcription of specific sets of genes.

Cell surface receptors and ion channels are among the cell surface proteins that respond to extracellular signals and initiate the events that lead to this varied gene expression and response. Ion channels and cell surface-localized receptors are ubiquitous and physiologically important cell surface membrane proteins. They play a central role in regulating intracellular levels of various ions and chemicals, many of which are important for cell viability and function.

Cell Surface Receptors

Cell surface-localized receptors are membrane spanning proteins that bind extracellular signalling molecules or changes in the extracellular environment and transmit the signal via signal transduction pathways to effect a cellular response. Cell surface receptors bind circulating signal molecules, such as cytokines, growth factors and hormones, etc., as the initiating step in the induction of numerous intracellular pathways. Receptors are classified on a structural basis or on the basis of the particular type of pathway that is induced. Among these classes of receptors are classes of cytokine receptors which include those that bind growth factors and have intrinsic tyrosine kinase activity, such as the heparin binding growth factor (HBGF) receptors, the immunoglobulin receptor superfamily, the hematopoietin/cytokine receptor superfamily, the nerve-growth factor receptor superfamily, other receptor tyrosine or serine kinases, and those that couple to effector proteins through guanine nucleotide binding regulatory proteins, which are referred to as G protein coupled receptors and G proteins, respectively.

Cytokines are intercellular messengers which coordinate communication between cells within a particular tissue, for example, antibody and T cell immune system interactions, and serve to modulate or modify the biological response. They are pleiotropic and have a broad spectrum of biological effects on more than one type of cell or tissue. The receptors for cytokines are broadly grouped into two classes, where the Class I cytokine receptors include receptors that bind various interleukins (IL-2, IL-3, IL-4, IL-6, IL-7, IL-9, IL-11, IL-12, IL-15), erythropoietin (EPO), growth hormone (GH), granulocyte colony stimulating factor (G-CSF), granulocyte macrophage colony stimulating factor (GM-CSF), leukemia inhibitory factor (LIF), and ciliary neurotrophic factor (CNTF), and the Class II cytokine receptors include receptors that bind interferon (IFN) $\alpha/\beta$, IFN$\gamma$, and IL-10.

Interferon Receptors

Human interferons (IFNs) are a family of homologous helical cytokines composed of three distinct classes: type I, type II, and type III based on nucleotide and amino acid sequence homology. Human Type I IFNs consist of IFN-$\alpha$, IFN-$\beta$, IFN-$\epsilon$, IFN-$\kappa$, and IFN-$\omega$. Human IFN-$\alpha$ includes a group of closely related proteins encoded by at least 12 functional IFN-$\alpha$ genes. IFN-$\beta$, IFN-$\epsilon$, IFN-$\kappa$, and IFN-$\omega$, are encoded by single more distantly related genes. Type II IFN, or IFN$\gamma$, is encoded by an unrelated gene and binds to a distinct cell surface receptor (De Maeyer et al., 1988; Pestka et al., 1987 and Diaz et al., 1993). Recently, a novel group of interferons designated IFN-$\lambda$ or type III IFNs has been described. The group has three members IFN-$\lambda$1, IFN-$\lambda$2, and IFN-$\lambda$3 also termed interleukin-29 (IL-29) ($\lambda$1), and IL-28A/B ($\lambda$2/3). (Sheppard et al., 2003; and Ank et al., 2006).

Type I IFNs bind to a common receptor, as shown by their ability to cross-compete for receptor binding (Pestka et al., 1987; Branca et al., 1981; and Merlin et al., 1985). The Type 1 interferon receptor has the largest number of natural ligands, some 14 in all, of all known cytokine receptors. Binding of interferons to their cell surface receptor represents the initial and probably most specific step in the IFN signaling pathway.

The Type I IFN receptor is composed of two transmembrane glycoproteins, IFNAR1 and IFNAR2 (Uze et al., 1990; Novick et al., 1994; Lutfalla et al., 1995; Domanski et al., 1995), which are rapidly tyrosine-phosphorylated following IFN binding (Platanias et al., 1994; Constantinescu et al., 1994; and Abramovich et al., 1994). Both subunits belong to the class II cytokine receptor superfamily (Bazan et al., 1990 and Thoreau et al., 1990) and are required for high affinity ligand binding and the establishment of biological activity (Langer et al., 1996 and Domanski et al., 1996). Class II cytokine receptors are distinguished from Class I receptors on the basis of the pattern of the conserved pairs of cysteine residues that are thought to form disulfide bonds.

The Type II IFN (IFN $\gamma$) receptor is composed of two transmembrane glycoproteins, IFNGR1 and IFNGR2 that are preassembled at the cell surface. Binding of IFN $\gamma$ to its receptor activates the tyrosine kinases Jak1 and Jak2 resulting in tyrosine-phosphorylation and formation of a Stat1 homodimer. The activated Stat1 homodimer is then translocated to the nucleus where it binds to the GAS (Gamma Activated Sequence) resulting in transcriptional activation of IFN γ activated genes.

Type III interferons bind to a unique receptor comprising the IL-28Rα, which is specific for a chain of the IFN-λs, and the IL-10Rβ chain which is also part of the receptors for IL-10, IL-22, and IL-26 (Ank et al, 2006).

In contrast to other cytokine receptors, particularly the IFN-γ receptor, neither IFNAR1 nor IFNAR2 alone bind to IFNα or IFNβ with an affinity comparable to the heterodimer. Despite the fact that IFNAR2 plays a prominent role in ligand binding, IFNAR1 contributes to IFN binding by increasing the affinity of the receptor complex (4-10 fold) relative to that of IFNAR2 alone. IFNAR1 also modulates the specificity of ligand binding relative to that observed with IFNAR2 alone (Cohen et al., 1995; Russell-Harde et al., 1995; Cutrone et al., 1997; and Cook et al., 1996). IFNAR1 has a larger extracellular domain than most other class II cytokine receptors, composed of 4 immunoglobulin-like subdomains separated by di- or tri-proline motifs which can be divided into two tandem repeats (Novick et al., 1994; Lutfalla et al., 1992; and Uzé et al., 1995).

Human, murine and bovine IFNAR1 have been cloned and expressed in human and murine cells. Studies performed with transfected cells show that IFNAR1 plays a central role in ligand binding, cellular responses to IFNs and in the induction of the biological activities of the Type I interferons (Novick et al., 1994; Abramovich et al., 1994; Uzé et al., 1992; Mouchel-Vielh et al., 1992; Lim et al., 1993; Cleary et al., 1994; Constantinescu et al., 1995; Hwang et al., 1995; Vandenbroek et al., 1995; and Colamonici et al., 1994). The IFN receptor also determines the high degree of species specificity characteristic of the IFNs. Thus, transfection of mouse cells with IFNAR1 and IFNAR2 renders mouse cells sensitive to human type I IFNs since both human and mouse cells share a common signaling pathway and common IFN responsive elements in the promoter regions of IFN regulated genes. Furthermore, the intracellular domain of IFNAR1 has been shown to play a key role in the transduction of the signal initiated at the cell surface by binding of Type I interferons to the nucleus (Basu et al., 1998). Targeted disruption of the IFNAR1 gene results in the loss of the antiviral response to Type I IFNs demonstrating that this receptor polypeptide is an essential component of the receptor complex and that both IFNAR1 and IFNAR2 subunits are required for IFNα and IFNβ signaling (Vandenbroek et al., 1995; Muller et al., 1994; Fiette et al., 1995; Steinhoff et al., 1995; and van den Broek et al., 1995).

Binding of type I interferon to the receptor complex activates two Janus kinases, Tyk2 and JAK1, which mediate the tyrosine phosphorylation and activation of two latent cytoplasmic transcription factors STAT1 and STAT2 which form a complex (ISGF3) with a p48 DNA binding protein, interferon responsive protein 9 (IRF 9), which is translocated to the nucleus to promote specific gene transcription (Fu et al., 1992; Schindler et al., 1992; Darnell et al., 1994; Ihle et al, 1995; and Taniguchi, 1995). Both Tyk2 and STAT2 are constitutively associated with the membrane proximal region of the IFNAR1 chain, while JAK1 and STAT1 are physically associated with IFNAR2 and all four factors are rapidly activated during IFNα stimulation (Lutfalla et al., 1995; Bazan, 1990; Basu et al., 1998; Barbieri et al., 1994; Velazquez et al., 1995; Uddin et al., 1995; Yan et al., 1996(a) and 1996(b).

Binding of type III IFNs to their cell-surface receptor also activates the ISGF3 complex suggesting that type III IFNs also activate a number of genes in common with type I IFNs (Ank et al., 2006).

Key populations of cells including DCs distributed throughout the peripheral tissues act as sentinels capable of recognizing infectious agents through pattern-recognition receptors (PRR). These include the Toll-like receptor (TLR) family of cell surface and endosomal membrane receptors (Uematsu and Akira, 2007) and the retinoic acid-inducible gene I (RIG-I)-like cytosoloic receptor proteins RIG-I, MDA5, and LGP2 (Yoneyama and Fujita, 2007). Thirteen members of the TLR family have been identified in mammals (Uematsu and Akira, 2007). Each TLR mediates a distinctive response in association with different combinations of four Toll/IL-1 receptor (TIR) domain-containing adaptor proteins (MyD88, TRIP, TIRAP/MAL, and TRAM). All the TLRs except TLR3 interact with MyD88. TLR3, which recognizes single-stranded or double-stranded viral RNA, is localized in the endosomes of myeloid DCs and requires acidification of vesicles for activation. TLR3 signals via TRIF and activates TBK1/IKKe which phosphorylates the interferon regulatory factor 3 (IRF3) and NFkB, resulting in production of IFN b (Hemmi et al, 2004, Perry et al., 2004). The RIG-1-like receptor proteins are DExD/H box RNA helicases two of which, RIG-I and MDA5, carry caspase activation and recruitment domain (CARD)-like motifs at the N-terminus (Yoneyama and Fujita, 2007). The CARD domain interacts with IPS-1 resulting in activation of IRF3 and NFkB and production of IFN b. Thus, activation of PRRs leads to the production of pro-inflammatory cytokines including type I IFNs and activation of the innate immune response. Dendritic cells signal principally through TLRs while RIG-1-like receptors predominate in other cell types. Two major DC sub-sets can be distinguished in man, CD11c(+) monocyte derived myeloid DCs, present in most tissues, and CD11c(−) plasmacytoid DCs (pDCs), present principally in lymph nodes. Plasmacytoid DCs are the principal producers of type I IFNs in response to viruses (Steinmann and Hemmi, 2006). Plasmacytoid DCs express high levels of TLR7/8 and TLR9 that recognize single-stranded RNA (ssRNA) and CpG DNA respectively (Diebold et al., 2004, Heli et al., 2004). Hemmi et al., 2000). Activation of both TLR7/8 and TLR9 leads to the formation of a complex with MyD88 and phosphorylation of IRF7 and production of high levels of type I IFNs (Uematsu and Akira, 2007).

TNF Receptors

Tumor necrosis factor alpha (TNF-α) is a multifunctional cytokine that exerts pleiotropic effects on different cell types. TNF-α is synthesized as pro-TNF, a 26 kDa membrane bound protein, which is released upon cleavage of its pro domain by TNF-converting enzyme (TACE) to yield a 17 kDa protein consisting of 157 amino acids that exists as a homotrimer in solution. TNF-α bind to two distinct receptors TNFR-1 (p55) and TNFR2 (p75). TNFR1 contains a death domain (absent from TNFR2) which is involved in the induction of apoptosis. Binding of the TNF-α homotrimer to TNFR-1 results in trimerization of TNFR-1 and the silencer of death domain (SODD) is released. The TNFR-associated death domain (TRADD) binds to the death domain of TNFR-1 and recruits the adaptor proteins, receptor interacting protein (RIP), TNFR-associated factor 2 (TRAF-2), and the Fas-associated death domain (FADD). TNFR-1 signals apoptosis, by FADD binding pro-caspase-8 the activation of which leads to induction of a protease cascade resulting in apoptosis. TNFR-1 signals survival by recruitment of TRAF-2 which inhibits apoptosis via the cytoplasmic inhibitor of apoptosis protein (cIAP). One of the principal signaling pathways triggered by recruitment of TRAF-2 and RIP to the TNFR-1 receptor complex is the NF-κB pathway which transduces a signal to the nucleus culminating in transcriptional activation of a number of TNF target genes (Schwamborn et al., 2003). NF-κB is a ubiquitous transcription factor induced by a number of cytokines (including IFNγ, IL2, IL5 and IFNα2). NF-κB is involved in the regulation of numerous genes involved in processes including, the inflammatory response, apoptosis, cancer, neuronal survival, and innate immunity. Activation of NF-κB is controlled principally at the posttranscriptional level by degradation of the inhibitory subunit IκB of the p55/p65/IκB complex present in the cytoplasm. Activating stimuli such as TNFα activate a kinase complex composed of two IκB-specific kinases (IKKα and IKKβ) and a modulatory subunit (NEMO or IKKγ). This leads to phosphorylation of the inhibitory subunit, which is then ubiquitinylated and degraded via the proteasome. This triggers translocation of NF-κB into the nucleus, where it initiates transcription by binding to regulatory sequences (NF-κB recognition/binding sequences) present in the promoter region of NF-κB target genes.

G-Coupled Receptors

The G protein transmembrane signaling pathways consist of three proteins: receptors, G proteins and effectors. G proteins, which are the intermediaries in transmembrane signaling pathways, are heterodimers and consist of α, β and γ subunits. Among the members of a family of G proteins the α subunits differ. Functions of G proteins are regulated by the cyclic association of GTP with the α subunit followed by hydrolysis of GTP to GDP and dissociation of GDP.

G protein coupled receptors are a diverse class of receptors that mediate signal transduction by binding to G proteins. Signal transduction is initiated via ligand binding to the cell membrane receptor, which stimulates binding of the receptor to the G protein. The receptor G protein interaction releases GDP, which is specifically bound to the G protein, and permits the binding of GTP, which activates the G protein. Activated G protein dissociates from the receptor and activates the effector protein, which regulates the intracellular levels of specific second messengers. Examples of such effector proteins include adenyl cyclase, guanyl cyclase, phospholipase C, and others.

Growth Factors and Growth Factor Receptors

Polypeptide growth factors are modulators of cell proliferation and differentiation whose biological functions are mediated by the interaction of the growth factor with cell surface receptors and subsequent alterations in gene expression. Growth factors bind to specific receptors and appear to induce tyrosine phosphorylation and c-fos mRNA synthesis. In addition, at least some growth factors, such as platelet-derived growth factor (Yeh et al., 1987) and heparin-binding growth factor-2 or basic fibroblast growth factor (Bouche et al., 1987), are translocated to the nucleus.

Activation of growth factor receptors by interaction with specific growth factors or with agents such as phorbol mistric acetate (PMA) activates protein kinase C, which is a family of phospholipid- and calcium-activated protein kinases. This activation results in the transcription of an array of proto-oncogene transcription factor encoding genes, including c-fos, c-myc and c-jun, proteases, protease inhibitors, including collagenase type I and plasminogen activator inhibitor, and adhesion molecules, including intercellular adhesion molecule I. Protein kinase C activation antagonizes growth factor activity by the rapid phosphorylation of growth factor receptors, which thereby decreases tyrosine kinase activity. Growth factors and other mitogens that induce cell proliferation and cell growth are believed to play a role in tumor growth, which often carry identifiable cell surface receptors specific for growth factors and other extracellular signals.

The interaction of nerve growth factor (NGF) with its receptor is typical of the array of responses such an extracellular signal induces. NGF is a polypeptide growth hormone that is necessary for differentiation and growth of the neural crest-derived sensory neuron. NGF binds to its specific cell surface receptor and is retrogradely transported to the cell body (Changelian et al., 1989). This initiates a cascade of intracellular events, culminating in a differentiated phenotype. PC12 cells, which are a rat pheochromocytoma cell line, are used as a model for the study of NGF-mediated differentiation. When treated with NGF, PC12 cells change from replicating adrenal-chromaffin-like cells to nonreplicating, electrically excitable sympathetic-neuron-like cells.

Concomitant with the phenotypic changes, there is induction and expression of specific genes. Binding of NGF to PC12 cells induces the immediate and rapid expression of certain genes, including the c-fos, NGF1-A and NGF1-B genes, which are referred to as early genes. Such early genes are believed to encode transcriptional regulators. The NGF-1A gene product contains tandemly repeated "zinc finger" domains that are characteristic of DNA-binding proteins, and the NGF1-B protein is homologous to members of the glucocorticoid receptor family and, thus, may function as a ligand-dependent modulator of transcription. The c-fos gene product, FOS appears to function as a transcriptional regulatory molecule.

The c-fos Gene and Related Genes

As discussed above, induction of expression of the c-fos gene is an event that is common to a number of response pathways that are initiated by the activity of a variety of cell surface proteins.

The c-fos gene product, FOS, associates with the transcription activator JUN, which is the product of the c-jun gene, to form a complex that forms a transcription activation complex, AP-1. Transcription of both c-fos and c-jun is induced rapidly and transiently following stimulation. The induced mRNAs accumulate for 1-2 hours in the cytoplasm where the FOS and JUN proteins, which are short-lived, are translated and then translocated to the nucleus to form a heterodimeric protein complex that binds to the DNA regulatory element, AP-1 binding site.

The c-fos and c-jun genes are members of gene families that encode proteins that participate in the formation of heterodimeric complexes that interact with AP-1 binding sites. Transcription factor AP-1 is composed of several protein complexes whose concentrations change upon cell stimulation. These complexes specifically interact with a seven-base core nucleotide sequence motif, that is known to be a relatively common constituent of both positive and negative transcriptional regulatory elements and that is required for both basal and induced levels of gene expression.

The gene products, FOS and JUN cooperate in the regulation of target genes that underlie many cellular and adaptive responses to the environment. They are involved in a number of neurophysiological processes.

Thus, c-fos induction involves distinct second messenger pathways that act via separate regulatory elements and that differentially modify, the resulting gene product, FOS, which in turn interacts in different ways with differentially modified JUN protein. Therefore, a multitude of extracellular events induce expression of a small number of inducible proteins that form an array of protein complexes that can differentially bind to DNA regulatory elements that contain AP-1 binding sites. Therefore, numerous cell surface proteins can act via overlapping transduction pathways and transduce extracellular signals that ultimately induce a variety of responses.

There are many assays that may rely on in vivo activity in a living cell line. One example is a cell line having an Interferon Stimulatory Response Element (ISRE) connected to a luciferase gene, or another reporter gene, so that when the cell line is subjected to the presence of interferon as an extracellular signal, the signal transduction activity of endogenous interferon cell surface receptors produces a signal that activates the ISRE, which then causes transcription of the luciferase gene. Thus, the activity of luciferase in creating light can be measured and is related to the amount of interferon which is present in the sample, and which is proportional to the amount of interferon over a particular range (Lallemand et al., 1996).

Lleonart et al. (1990) described a reporter gene assay for Type I interferon based on monkey Vero cells transfected with Type I interferon inducible mouse Mx promoter linked to the human growth hormone (hGH) gene as the reporter gene. This Type I interferon assay was developed further by transfecting monkey Vero cells with a plasmid carrying the luciferase reporter gene under the control of the Type I interferon inducible mouse Mx1 promoter (Canosi et al., 1996).

A further type of interferon reporter gene assay was developed by Hammerling et al. (1998) who used a human glioblastoma cell line transfected with a reporter gene construct of glial fibrillary acidic protein (GFAP) promoter and an *E. coli* β-galactosidase (lacZ) reporter gene. In this particular assay, it is the reduction/inhibition of β-galactosidase expression by either human Type I or Type II interferon in a selective and dose dependent manner that is measured.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It is an object of the present invention to develop a reporter gene containing cell line with increased specificity and/or sensitivity for a particular extracellular signal of interest (i.e., ligand) so that it can be used in a gene-reporter assay to accurately determine the presence and/or level of the extracellular signal of interest in the presence of other extracellular signals that are capable of activating the same signal transduction pathway as the extracellular signal of interest or capable of activating another signal transduction pathway capable of modulating the transcription of the reporter gene.

Thus, the present invention provides a cell line transformed with a reporter gene construct which includes a nucleotide sequence encoding a reporter gene product operatively linked to a transcription control element that is activated as part of the signal transduction pathway initiated by a first cell surface molecule or complex in response to a first extracellular signal (extracellular signal of interest). The signal transduction pathway includes a transcription factor that binds to the transcriptional control element so as to activate the transcriptional control element and thereby regulate transcription of the reporter gene. The sensitivity and/or specificity of the response of this cell line to the extracellular signal of interest is improved because:

a) the transcription control element is a modification of a naturally occurring transcriptional control element or is a synthetic transcriptional control element containing one or more recognition sequence(s) specific for the transcription factor, that is activated as part of the signal transduction pathway initiated by the first extracellular signal, such that the sensitivity and/or specificity of the transcriptional control element by increasing the number of recognition sequences specific for the transcription factor(s) of interest and/or by excluding recognition sequences for factors that are susceptible of reducing sensitivity or specificity for the extracellular signal of interest; and/or b) the cells of the cell line lack a second surface molecule that responds to, or is part of a complex that responds to, a second extracellular signal, which second extracellular signal, if the second cell surface molecule were present, would cause the initiation of a second transduction pathway that modulates the transcription of said reporter gene to decrease either the sensitivity or specificity of the response to the first extracellular signal.

The present invention also provides a cell based assay kit for determining with improved sensitivity and/or specificity the presence and/or level in a sample of an extracellular signal of interest that activates the signal transduction activity of a cell surface molecule or complex.

Further provided by the present invention is a gene-reporter assay for determining the presence and/or level in a sample of an extracellular signal of interest (i.e., ligand).

DETAILED DESCRIPTION OF THE INVENTION

Figure 1:
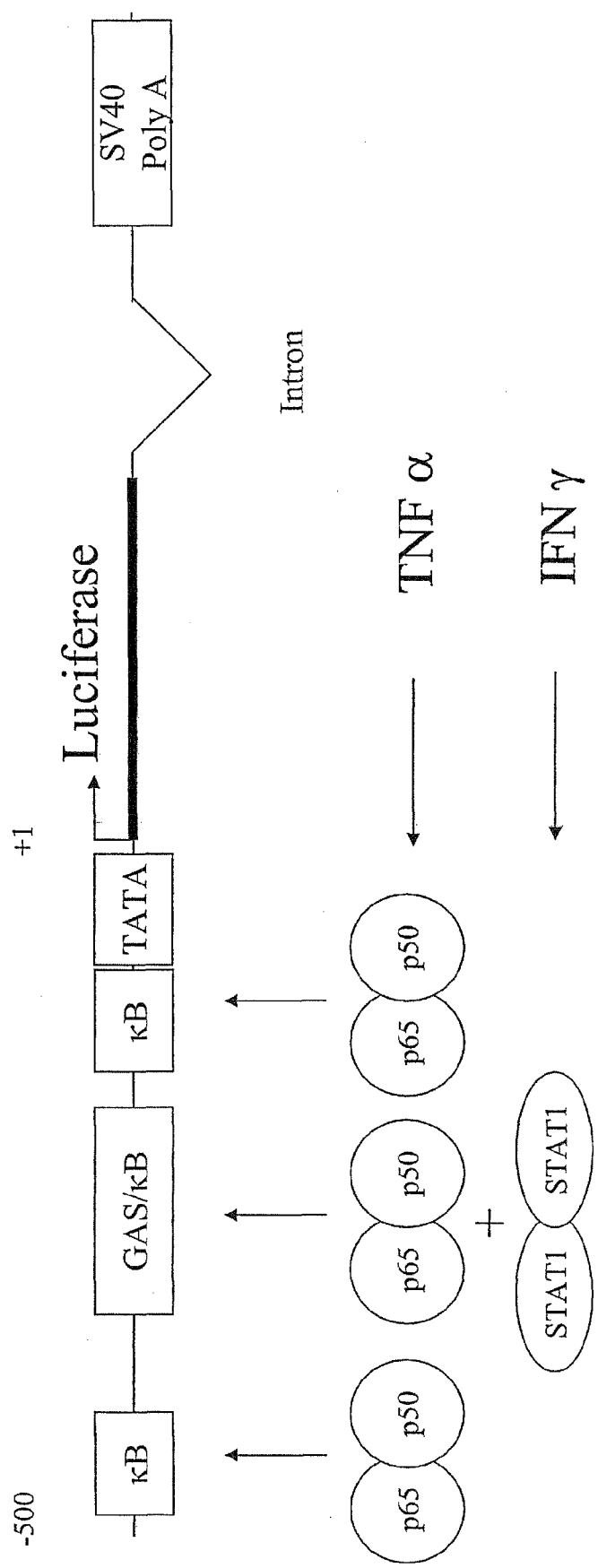
FIG. 1 is a schematic illustration of an initial reporter gene construct with the −500 to +1 nucleotides of the promoter region of the Interferon Response Factor (IRF-1) gene cloned upstream of the firefly luciferase reporter gene to regulate the transcription of firefly luciferase.

The present inventors have developed and established a gene-reporter assay using a cell line transfected with a gene-reporter construct such that the ensemble is capable of detecting and responding to low levels of an extracellular signal (i.e., ligand) in a highly specific manner, thus allowing quantification of the extracellular signal. In a preferred embodiment, this was obtained by using a synthetic chimeric promoter, containing an optimal number of response elements specific for transcription factors induced by the extracellular signal of interest and lacking response elements for transcription factors activated by unrelated extracellular signals (i.e., ligands), to drive a minimal promoter and regulate the expression of a reporter gene. A further level of specificity is obtained by transfecting cells carrying a specific receptor for the extracellular signal of interest but lacking receptors for other extracellular signals capable of activating the same signal transduction pathway as the extracellular signal of interest or capable of activating another signal transduction pathway capable of modulating the transcription of the reporter gene via interaction with the extracellular signal-specific response elements regulating the synthetic promoter. Such an ensemble preferably also improves the level of sensitivity in detecting the extracellular signal of interest.

The term "specificity" as used herein is the ability of a gene-reporter assay to recognize a particular extracellular signal of interest without interference from other extracellular signals. The term "sensitivity" as used herein is the ability of a gene-reporter assay to detect low amounts of an extracellular signal of interest that would be otherwise undetectable in an assay that is less "sensitive" to the extracellular signal.

Most preferably, the cell line according to the present invention is one where the cell line is both a) transformed with a reporter gene construct where the sensitivity and/or specificity of a transcriptional control element operatively linked to the reporter gene is improved by modification of a naturally occurring transcriptional control element or a synthetic promoter containing an optimum number of control elements specific for transcription factor(s) induced by the extracellular signal of interest, and b) lacking a functional second cell surface molecule or complex that responds to other extracellular signals which would otherwise interfere with a first extracellular signal of interest by causing initiation of a signal transduction pathway that modulates the transcription of the reporter gene in order to improve the sensitivity and/or specificity of the cell line to the extracellular signal of interest. It is contemplated that the cell line may lack more than one functional cell surface molecule or complex depending on how many other cell surface molecules or complexes need be absent/inactive in the cell line to prevent interference from other extracellular signals in a gene-reporter assay with the extracellular signal of interest. The lack of one or more functional cell surface molecules or complexes (i.e., receptors and receptor complexes) in the cell line may be naturally occurring or may be obtained by techniques such as "knock out" by inactivating the gene(s) encoding the cell surface molecule(s) or by silencing ("knock down") of the gene(s) encoding the cell surface molecule(s) using RNA interference (RNAi).

The cell surface molecule from which its signal transduction activity, in response to an extracellular signal, regulates the expression of a reporter gene product can be any cell surface protein that is known to those of skill in the art or that may be identified by those of skill in the art. Exemplary cell surface proteins include, but are not limited to, cell surface receptors and ion channels. Non-limiting examples of cell surface receptors include cytokine receptors (e.g., receptors for Type I interferon, Type II interferon, tumor necrosis factor (TNF), interleukins, growth hormone, erythropoietin (EPO), granulocyte colony stimulating factor (G-CSF), granulocyte macrophage colony stimulating factor (GM-CSF), leukemia inhibitory factor (LIF), ciliary neurotrophic factor (CNTF), etc.), growth factor receptors, hormone receptors, T cell receptors, antigen receptors, complement receptors, death receptors, and neuroreceptors. The reference text, J. M. Cruse and Robert E. Lewis, *Atlas of Immunology*, CRC Press, Washington, D.C., 1999, which discloses many receptors involved in immune response and immune system interactions is entirely incorporated herein by reference. Cell surface receptors also include, but are not limited to, TNF receptors (e.g. TNFα) muscarinic receptors (e.g., human M2 (GenBank accession #M16404); rat M3 (GenBank accession #M16407); human M4 (GenBank accession #M16405); human M5 (Bonner et al., 1988); and the like); neuronal nicotinic acetylcholine receptors (e.g., the α2, α3 and β2 subtypes); the rat α2 subunit (Wada et al., 1988); the rat α3 subunit (Boulter et al., 1986); the rat α4 subunit (Goldman et al., 1987); the rat α5 subunit (Boulter et al., 1990); the rat β2 subunit (Deneris et al., 1988); the rat β3 subunit (Deneris et al., 1989); the rat β4 subunit (Duvoisin et al., 1989); combinations of the rat α subunits, β subunits and α and β subunits; GABA receptors (e.g., the bovine α1 and β1 subunits (Schofield et al., 1987); the bovine α2 and α3 subunits (Levitan et al., 1988); the γ-subunit (Pritchett et al., 1989); the β2 and β3 subunits (Ymer et al., 1989); the δ subunit (Shivers, B. D., 1989); and the like); glutamate receptors (e.g., receptor isolated from rat brain (Hollmann et al., 1989); and the like); adrenergic receptors (e.g., human β1 (Frielle et al., 1987); human α2 (Kobilka et al., 1987); hamster β2 (Dixon et al., 1986); and the like); dopamine receptors (e.g., human D2 (Stormann et al., 1990); rat (Bunzow et al., 1988); and the like); NGF receptors (e.g., human NGF receptors (Johnson et al., 1986); and the like); serotonin receptors (e.g., human 5HT1a (Kobilka et al., 1987); rat 5HT2 (Julius et al., 1990); rat 5HT1c (Julius et al., 1988); and the like).

Also included as nominally cell surface receptors are the extracellular and/or intracellular Toll-like receptors and intracellular receptors such as RIG-1 or MDA5, because such receptors detect extracellular signals, such as a viral or bacterial particles or components that in the case of the intracellular Toll-like receptors, interact with these Toll-like receptors after endocytosis from the cell surface. Such Toll-like (TLR) cell surface or endosomal membrane receptors (Uematsu and Akira, 2007), or the retinoic acid-inducible gene 1 (GIG-I)-like cytosolic receptor proteins RIG-I, MDA5 and LGP2 (Yoneyama and Fujita, 2007) are non-limiting examples of pattern recognition receptors.

Ion channels include, but are not limited to, calcium ion channels (e.g., human neuronal α2 subunit (see WO89/09834); rabbit skeletal muscle α1 subunit (Tanabe et al. 1987); rabbit skeletal muscle α2 subunit (Ellis et al., 1988); rabbit skeletal muscle β subunit (Ruth et al., 1989); rabbit skeletal muscle γ subunit (Jay et al., 1990); and the like); potassium ion channels (e.g., rat brain (BK2) (McKinnon, D., 1989); mouse brain (BK1) (Tempel et al., 1988); and the like); sodium ion channels (e.g., rat brain I and II (Noda et al., 1986); rat brain III (Kayano et al., 1988); and others).

It will be appreciated by those of skill in the art that the cell surface protein discussed above is preferably endogenous to the cell line of the present invention. However, it will also be appreciated that the cell surface protein may be expressed from cloned DNA, such as to supplement the number of the cell surface protein at the surface of the cell, or the cell surface protein may be expressed from cloned DNA but is a cell surface protein that is heterologous to the host cell.

For signal transduction, the intracellular signal that is transduced is initiated by the specific interaction of an extracellular signal, i.e., a molecule or a change in the extracellular environment (such as light, UV-irradiation, or γ-irradiation), with a cell surface molecule or complex, receptor or ion channel present on the cell surface. This interaction sets in motion a cascade of intracellular events, the ultimate consequence of which is a rapid and detectable change in the expression of a gene product, which in the cell of the present invention is a reporter gene product. The extracellular signal or effector molecule is any compound or substance that in some manner specifically alters the activity of a cell surface molecule or a complex of cell surface molecules (i.e., receptor complexes). Examples of such signals include, but are not limited to, molecules such as cytokines (i.e., interferons), growth factors, hormones, endorphins, neurotransmitters, acetylcholine, and mitogenic substances, such as phorbol mistric acetate (PMA), that bind to cell surface receptors and ion channels and modulate the activity of such receptors and channels. For example, antagonists are extracellular signals that block or decrease the activity of cell surface protein and agonists are examples of extracellular signals that potentiate, induce or otherwise enhance the activity of cell surface proteins.

The reporter gene construct carried by the cell line of the present invention is a DNA molecule that includes a nucleotide sequence encoding a reporter gene product operatively linked to transcriptional control elements/sequences. Transcription of the reporter gene is controlled by these sequences. The activity of at least one or more of these control sequences is directly or indirectly regulated by the cell surface molecule or complex. The transcriptional control sequences include but are not limited to promoters and other regulatory regions, such as enhancer sequences and repressor and activator binding sites, e.g., for binding a transcription factor such as NFκB, that modulate the activity of the promoter, or control sequences that modulate the activity or efficiency of the RNA polymerase that recognizes the promoter, or control sequences that are recognized by effector molecules, including those that are specifically induced by interaction of an extracellular signal with a cell surface protein. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional control elements or sequences. In addition, the construct may include sequences of nucleotides that alter translation of the resulting mRNA, thereby altering the amount of reporter gene product expressed.

A promoter that is regulated or modulated by the activity of a cell surface molecule or complex is a promoter whose activity changes when a cell is exposed to a particular extracellular signal by virtue of the presence of cell surface molecules or complexes whose activities are affected by the extracellular signal. For example, the c-fos promoter is specifically activated upon the specific interaction of certain extracellular signals, such as growth hormones, with a cell surface molecule, such as a growth hormone receptor. In particular, the regulation of such promoters by the cell surface molecule or complex, though indirect, occurs within minutes of the interaction of the cell surface molecule or complex with the extracellular signal. As used herein, operative linkage refers to the linkage of a transcriptional control element, i.e., promoter and/or transcription factor binding site, to a nucleotide coding sequence such that the transcriptional control element is properly positioned for its activity of binding RNA polymerase and initiating transcription of the nucleotide coding sequence. Thus, a nucleotide coding sequence in operative linkage with a promoter, is downstream with respect to the direction of transcription from the promoter, is in the correct reading frame with respect to the transcription initiation site and is inserted in a manner such that transcription elongation proceeds through the nucleotide coding sequence.

Suitable transcriptional control elements may be obtained or derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (Sheng et al., 1990), such as c-fos. Immediate early genes are genes that are rapidly induced upon binding of a ligand to a cell surface protein. The transcriptional control elements that are preferred for use in the reporter gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular stimulation, induction that is transient and independent of new protein synthesis, subsequent shut-off of transcription requires new protein synthesis, and mRNAs transcribed from these genes have a short half-life. It is not necessary for all of these properties to be present.

Suitable promoters and transcriptional control elements include, but are not limited to, the IFN Gamma Activated Sequence (GAS) from the Interferon Regulatory Factor 1 (IRF-1) gene, SV40 or other minimal promoters in combination with transcriptional control elements such as activator or transcription factor binding sequences (such as for NFκB), the vasoactive intestinal peptide (VIP) gene promoter (cAMP responsive; Fink et al., 1988); the somatostatin gene promoter (cAMP responsive; Montminy et al., 1986); the proenkephalin promoter (responsive to cAMP, nicotinic agonists, and phorbol esters; Comb et al. 1986); the phosphoenolpyruvate carboxy-kinase gene promoter (cAMP responsive; Short et al., 1986); the NGFI-A gene promoter (responsive to NGF, cAMP, and serum; Changelian et al., 1989); the transcriptional control elements obtained or derived from the c-fos gene; and others that may be known to or prepared by those of skill in the art.

The c-fos proto oncogene is the cellular homologue of the transforming gene of FBJ osteosarcoma virus. It encodes a nuclear protein that is most likely involved in normal cellular growth and differentiation. Transcription of c-fos is transiently and rapidly activated by growth factors and by inducers of other cell surface proteins, including hormones, differentiation-specific agents, stress, mitogens and other known inducers of cell surface proteins. Activation is protein synthesis independent. The c-fos regulatory elements include a TATA box that is required for transcription initiation, two upstream elements for basal transcription, and an enhancer, which includes an element with dyad symmetry and which is required for induction by TPA, serum, EGF, and PMA. The 20 bp transcriptional enhancer element located between −317 and −298 bp upstream from the c-fos mRNA cap site, is essential for serum induction in serum starved NIH 3T3 cells. One of the two upstream elements is located at −63 to −57 and it resembles the consensus sequence for cAMP regulation.

Preferably, the transcriptional control element is a synthetic chimeric promoter that contains a minimal promoter, which is most preferably the SV40 minimal promoter, and an optimal number of response elements specific for transcription factors induced by the extracellular signal of interest, but lacking response elements for transcription factors activated by unrelated extracellular signals.

In a preferred embodiment of the present invention, the cell line containing a reporter gene construct has both specificity and sensitivity for IFNγ as the extracellular signal. Current bioassays for IFN-γ are based for the most part on the ability of IFN-γ to inhibit virus replication (Ank et al., 2006) or inhibit cell proliferation (Sato et al., 2006). Such methods lack specificity since type I IFNs (IFN-α, IFN-β, IFN-ε, IFN-κ, and IFN-ω) also inhibit virus replication and cell proliferation. IFN-γ activity can also be assessed by its ability to induce NO in freshly isolated peritoneal exodate cells (Malu et al, 2003), kynurenine in WISH cells (Boyanova et al, 2002), or MHC class II antigens on susceptible cells (King, D. P., Jones, P. P., J. 1983). Such bioassays also lack specificity and are based upon cell culture systems that are inherently variable and give results that vary from assay to assay (Meager, 2006). Although a gene-reporter assay for IFN-γ based on induction of chloramphenicol acetyltransferase (CAT) activity has been developed the assay lacks specificity as it is also sensitive to type I IFNs (Lewis, 1995). Thus a gene-reporter assay that is specific and sensitive to low levels of IFNγ (Type II interferon) in the presence of Type I interferons (IFNα and β) is highly sought after in the art. However, because of degeneracy between GAS and ISRE consensus sequences and because of cross-talk between the STAT1-STAT2 heterodimer (from signal transduction pathway initiated at the IFNAR1/IFNAR2 Type I interferon receptor) and the STAT1-STAT1 homodimer (from signal transduction pathway initiated at the GAR1/GAR2 Type II interferon receptor), the presence of Type I interferons strongly interferes with gene-reporter assays for determining the level of IFNγ in a sample. Thus, a cell line containing a reporter gene construct with improved specificity and sensitivity for IFNγ would allow rapid determination of IFNγ levels in a sample. This capability of detecting the presence and/or determining the level of IFNγ, even in the presence of Type I interferon, would have immediate clinical application. For instance, the presence of IFNγ in cerebrospinal fluid is indicative of disease progression in relapsing remitting multiple sclerosis or other neurodegenerative diseases. Reduced production of IFN γ is also thought to be involved in the physiopathology of fibrotic disease such as idiopathic pulmonary fibrosis, systemic sclerosis, or scleroderma. Quantification of human IFN γ production can also be used as an in vitro marker of T-cell maturation/proliferation, the CD8+ CTL response, and NK cell activation. Quantification of IFN γ also provides the basis of a test for TB infection by measurement of T-cell proliferation in vitro in response to TB antigens. The presence of IFN γ in pleural effusion is diagnostic for extrapulmonary tuberculosis. Thus, with such a cell line in a gene-reporter assay for IFNγ, the need for a non-invasive diagnostic test is met.

The transcriptional control element, particularly as it relates to a preferred embodiment of the present invention where Type II interferon (IFNγ) is the extracellular signal, is preferably a gamma activated sequence (GAS). Regarding GAS, to which the STAT1 homodimer binds in genes responsive to Type II interferon, a consensus sequence, nnnsan ttccgGGAAntgnsn (SEQ ID NO:3; capital letters denote core sequence; underlines denote high conservation), from many selected binding sequences was identified (Horvath et al., 1995).

In the embodiment of the present invention where Type II interferon is the extracellular signal of interest (first extracellular signal) and Type I interferon (IFNα and IFNβ) is an interfering extracellular signal (second extracellular signal), a preferred transcriptional control element in the reporter gene construct is a Type II interferon responsive chimeric promoter in which GAS controls a SV40 minimal promoter operatively linked to a nucleotide sequence encoding a reporter gene product. Further in this embodiment of a cell line for use in a gene-reporter assay for IFNγ, the cell line has been selected for the lack of a functional type I IFN receptor, or cells have been genetically engineered to knock out the Type I interferon receptor (IFNAR1/IFNAR2), which is referred to generically in the "Summary of the Invention" section above as the second cell surface molecule. In the absence of a functional Type I interferon receptor, there is no STAT1-STAT2 heterodimer cross-talk to interfere with transcription activation from GAS in response to the STAT1 homodimer. Therefore, the specificity and sensitivity of the response to an IFNγ extracellular signal is markedly improved. Low levels of IFNγ can now be detected using the IFNAR1/IFNAR2 "knock out" cell line described above.

The term "knock out" as used herein relates to a cell line where a specific gene(s) has been inactivated, such as by a method of gene targeting. This is in contrast to the term "knock in" which as used herein relates to a cell line according to the present invention where a gene(s) for cell surface receptor or complexes or a portion thereof (i.e., at least the extracellular portion and elements required for the activation of the signal transduction pathway) from a first animal species is introduced ("knocked in") into the cell line of a second animal species. Such a "knocked in" cell surface receptor or complex can be used in the cell line for a gene-reporter assay when there is strict species specificity between the cell surface receptor or complex and its ligand, i.e., the cell surface receptor or complex which is endogenous to the cell line and which is an orthologue of the "knocked in" cell surface receptor does not (or negligibly) initiate a signal along its signal transduction pathway in response to a ligand of the "knocked in" cell surface receptor from another animal species.

The reporter gene product in the cell line of the present invention, whose level is a measure of the presence and/or the level of an extracellular signal that activates the signal transduction activity of a cell surface molecule, may be RNA or protein, as long as it is readily detectable. For instance, firefly luciferase, Renilla luciferase, Metridia secreted luciferase enhanced green fluorescent protein (EGFP) and jellyfish aequorin are most preferred embodiments of reporter gene products used according to the present invention. In the case of the enzyme firefly luciferase (dewet et al., 1987) and jellyfish aequorin (Rider et al., 2003), the result of its enzymatic activity, light, is detected and measured using a luminometer, whereas in the case of EGFP, a fluorescence activated cell sorter or analyzer (FACS) can be used at an appropriate wavelength to detect and quantify the amount of EGFP expressed in a cell. The distribution curve of the amount of luciferase, aequorin or EGFP expressed in a sample of cells will be determined by the amount of ligand (within a given range) to which the cell is exposed. Non-limiting examples of other suitable reporter gene products include dsRED, chloramphenicol acetyl transferase (CAT) (Alton et al., 1979) other enzyme detection systems, such as β-galactosidase, bacterial luciferase (Engebrecht et al., 1984 and Baldwin et al. 1984), alkaline phosphatase (Toh et al. 1989 and Hall et al. 1983), and bacterial or humanized β-lactamase (Zlokarnik et al., 1998).

The development of a gene-reporter assay specific for a pleiotropic cytokine is rendered difficult when signal transduction is mediated by a ubiquitous transcription factor induced by a number of unrelated cytokines and/or when the target genes activated by the cytokine are subject to a complex pattern of regulation. These difficulties can be obviated by the use of a synthetic chimeric promoter reporter gene construct lacking recognition sites for transcription factors activated by unrelated cytokines to transfect a cell line containing a ligand specific receptor but lacking receptors for other ligands which share a common signal transduction pathway with the ligand of interest. This approach is illustrated by reference to the pleiotropic cytokine TNFα that uses the NF-κB pathway to activate target genes. In a preferred embodiment of the present invention the cell line containing a reporter-gene construct has sensitivity and specificity for TNF-α.

TNF-α is a multifunctional pro-inflammatory cytokine that plays a key role in regulating apoptosis and cell survival and is involved in such important biological processes as inflammation, neoplastic transformation, and the immune response. Thus, TNF-α can be detected in the plasma of patients with Crohn's disease (Balog et al., 2004), in the plasma and synovial fluid of patients with rheumatoid arthritis (Marotte et al., 2005), and in the wound fluid of chronic non-healing wounds (Cowin et al., 2006. It is important therefore to be able to assess the relationship between the presence of TNF-α in a particular clinical sample and disease progression, or to determine the ability of anti-TNF-α therapies including anti-TNF-α antibodies (Remicade, Adlimumab) or a soluble TNF-α receptor (Enbrel) to block TNF-α activity. Conventional bioassays for TNF-α are based upon the ability of TNF-α to kill susceptible cell-lines (mouse L929 cells, WEHI 164 cells, or human HeLa cells) usually in the presence of an inhibitor of transcription such as actinomycin D or an inhibitor of translation such as cycloheximide. Alternatively the ability of TNF-α to up-regulate cellular adhesion molecules such as ICAM-1 (cellular adhesion molecule-1) can also be used as the basis of a bioassay for TNF-α. An obvious disadvantage of such methods is their lack of specificity. TNF-β, TRAIL, and TWEAK (Apo-3 ligand) all interfere with the TNF-α cytotoxicity assay and TNF-β, IL-1α, IL-1β, and IFN-γ all induce expression of ICAM-1 (Meager, 2006). Furthermore, such bioassays are based upon cell culture systems that are inherently variable and give results that vary from assay to assay (Meager, 2006). Although a gene-reporter assay for TNF-α, based on the activation of a NFκB regulated luciferase reporter gene construct, has been developed the assay lacks specificity as it is also sensitive to other agents that activate NFκB (McFarlane et al., 2002).

Binding of the TNF-α homotrimer to TNFR-1 results in trimerization of TNFR-1, recruitment of TRAF-2 and RIP to the TNFR-1 receptor complex, and activation of the NF-κB pathway culminating in transcriptional activation of a number of TNF target genes (Schwamborn et al., 2003). NF-κB is a ubiquitous transcription factor induced by a number of cytokines (including IFNγ, IL2, IL5 and IFNα2). NF-κB is involved in the regulation of numerous genes involved in processes including, the inflammatory response, apoptosis, cancer, neuronal survival, and innate immunity. Activation of NF-κB is controlled principally at the posttranscriptional level by degradation of the inhibitory subunit IκB of the p55/p65/IκB complex present in the cytoplasm. Activating stimuli such as TNFα activate a kinase complex composed of two IκB-specific kinases (IKKα and IKKβ) and a modulatory subunit (NEMO or IKKγ). This leads to phosphorylation of the inhibitory subunit, which is then ubiquitinylated and degraded via the proteasome. This triggers translocation of NF-κB into the nucleus, where it initiates transcription by binding to regulatory sequences (NF-κB recognition/binding sequences) present in the promoter region of NF-κB target genes.

TNFα target genes are subject to a complex pattern of regulation since NF-κB is a ubiquitous transcription factor induced by a number of cytokines. Furthermore, TNFα induces the expression of several NF-κB target genes which are themselves transcription factors including JunD and interferon regulatory factor-1 (IRF-1). Thus, enhanced transcription of IRF-1 for example is responsible for the cross-coupling of an interferon response with the TNF receptor mediated response. In order to construct a gene-reporter assay specific for the detection of TNFα such that cytokines other than TNFα (e.g., IFNγ, IL-2, IL-5, IL-6) which activate NF-κB would not interfere with the assay, a cell line that is receptor negative (i.e., naturally occurring, "knockout" or "knockdown") for the receptors of the principal extracellular activators of the NF-κB signaling pathway, other than TNFα, was transfected with a synthetic NF-κB regulated gene-reporter construct lacking recognition sites for transcription factors induced by unrelated cytokines.

Figure 4:
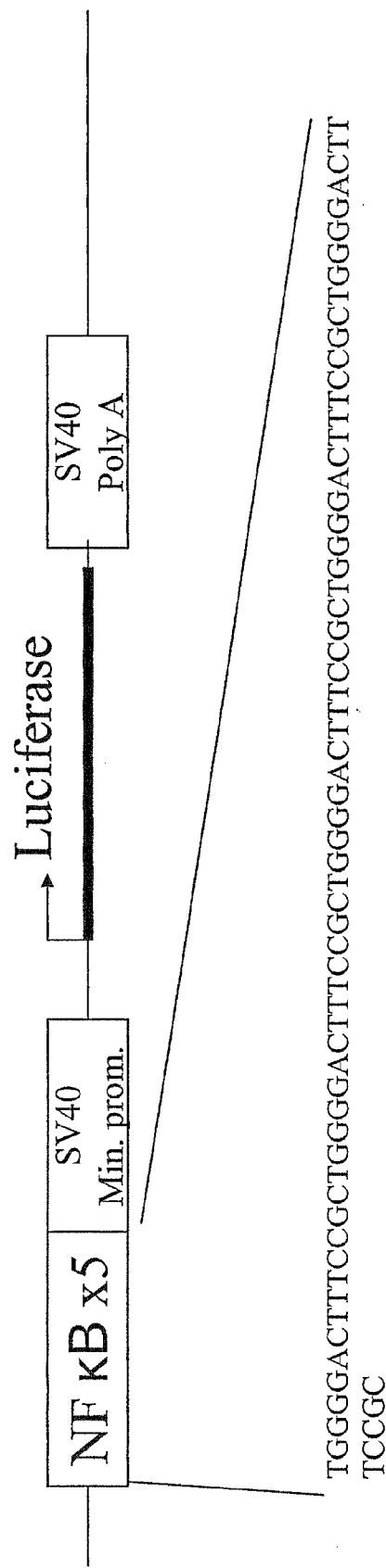
FIG. 4 is a schematic illustration of a reporter gene construct where a 5× tandem repeat of the canonical NFκB (SEQ ID NO:2) is positioned upstream of a SV40 minimal promoter to regulate the transcription of firefly luciferase.

Thus, a highly sensitive and reproducible method for quantifying TNFα activity has been developed by the present inventors as another preferred embodiment of the present invention. This preferred embodiment is based on the human T-cell line, Jurkat, transfected with the luciferase reporter gene controlled by a TNFα responsive chimeric promoter, which allows TNFα activity to be determined with a high degree of precision within a few hours. The TNFα responsive promoter used to transfect Jurkat cells is a synthetic promoter based on a tandem repeat of 5 canonical NFκB recognition sequences, the major TNFα responsive element for the principal transcription factor induced by TNFα (Imanishi et al., 2000). As tandem repeats of the canonical NFκB recognition/binding sequence were surprisingly found to be highly efficient ($10^5$ fold more) in enhancing transcription from a SV40 minimal promoter, a tandem repeat of 5 canonical NFκB recognition sequences was designed to confer maximal transcriptional activity on the synthetic promoter in response to TNFα treatment (FIG. 4). A stable clone, JUT-4, of transfected Jurkat cells was then selected on the basis of the maximum increase in relative luciferase units (RLU) in response to treatment with TNFα relative to untreated control cells. It will be appreciated that although the present inventors have found that tandem repeats of five canonical NFκB recognition/binding sequences are preferred, tandem repeats of more or less than five canonical NFκB recognition/binding are also contemplated.

Figure 2:
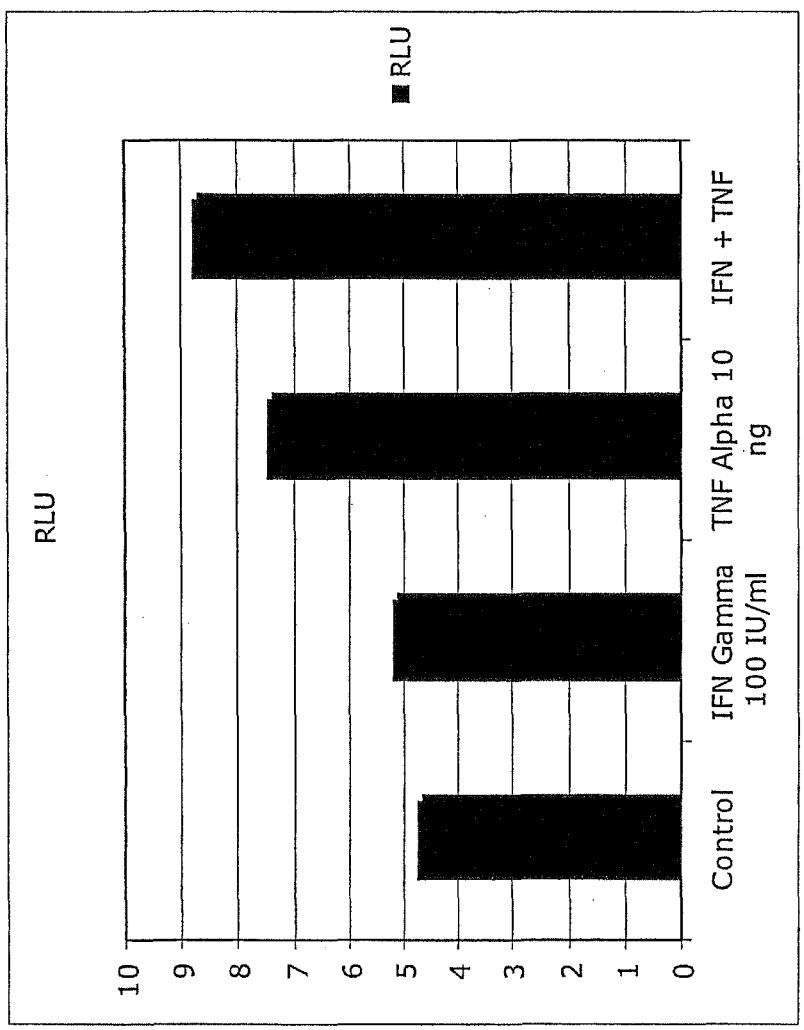
FIG. 2 is a graph showing relative luciferase units (RLU) of the initial reporter gene construct of FIG. 1 in response to IFNγ, TNFα, and IFNγ+TNFα.
Figure 5:
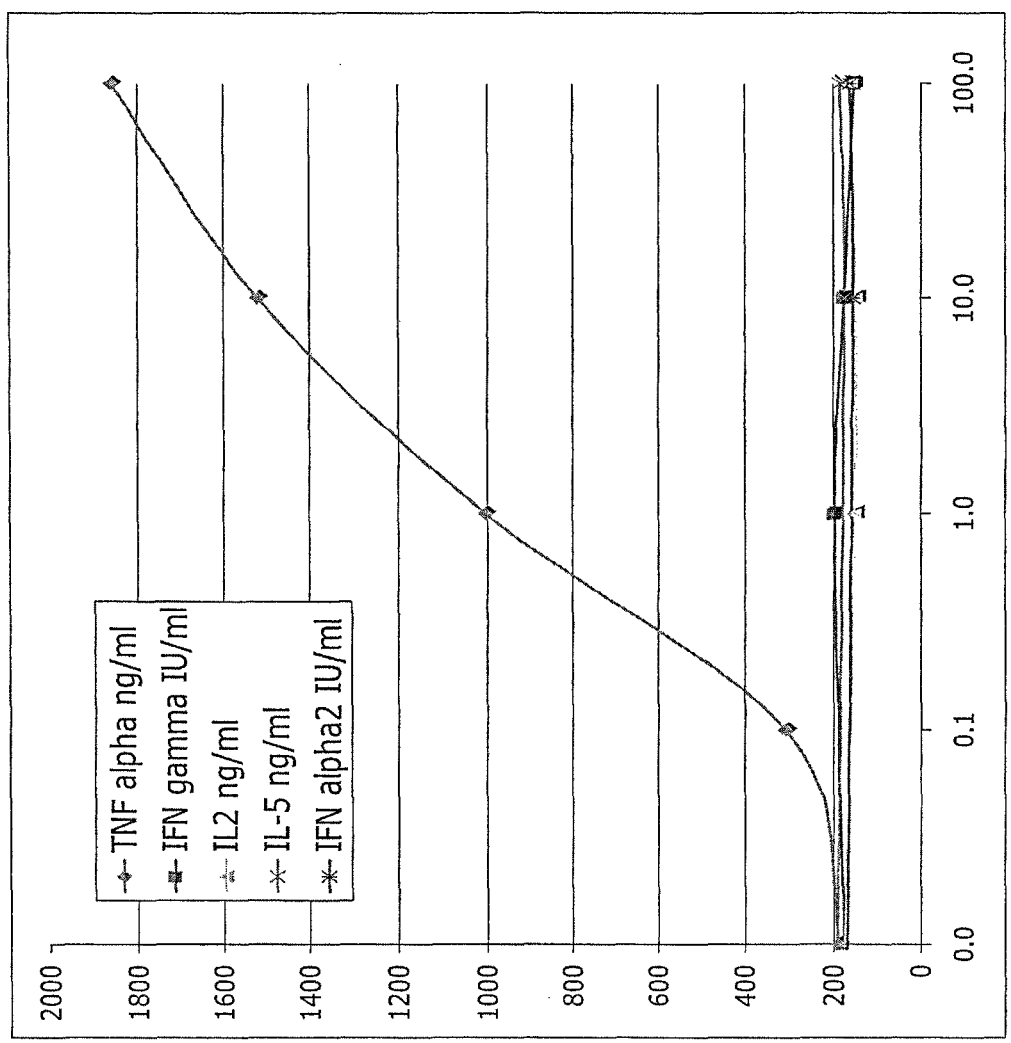
FIG. 5 is a graph showing relative luciferase units in a gene-reporter assay using the reporter gene construct of FIG. 4 in the presence of varying amounts of TNFα, IFNγ, IL2, IL5 and IFNα2.

FIG. 5 demonstrates that this preferred cell line embodiment, which is receptor negative for IFNγ and IL2 and which carries a reporter gene construct of tandem repeats of five canonical NFκB recognition sequences controlling a SV40 minimal promoter operatively linked to a luciferase coding sequence, is highly sensitive and specific for TNFα. The improvement in sensitivity and specificity for TNFα can be readily seen relative to a U937 cell line (has functional receptors for IFNγ and IL2) carrying a reporter gene construct in which the promoter region (−500 to +1) of the IRF-1 gene is operatively linked to the luciferase coding sequence (FIG. 1). This promoter region contains NFκB recognition sequences and a GAS sequence responsive to IFNγ. FIG. 2, shows that the reporter gene construct-transfected U937 cell line is responsive to both IFNγ and TNFα. When both IFNγ and TNFα are present, the sensitivity of the gene-reporter is reduced as the luciferase activity in RLU is less than the sum of the relative luciferase units (RLU) for IFNγ and TNFα assayed separately.

Other non-limiting examples of cell lines according to the present invention include cell lines containing, for example, the reporter gene construct shown in FIG. 4 but lacking functional cell surface receptors for at least TNFα and IFNγ (when a gene-receptor assay for IL2 is desired) and for at least TNFα, IFNγ and IL2 (when a gene-reporter assay for IL5 is desired).

Another aspect of the present invention is directed to an assay kit for determining the presence and/or level in a sample of a molecule that activates the signal transduction activity of a cell surface molecule or complex. This assay kit includes a plurality of cells of the cell line of the present invention (as a reagent) and a testing device having a plurality of wells. Preferably, the testing device is a multi-well microtiter plate, but can also be any type of receptacle, such as petri dishes or plates, with a plurality of wells in which an assay can be conducted to determine the level of a molecule in a sample. It is preferred that the cells as a component or reagent of the assay kit be disposed in the wells of the testing device, although it will be appreciated that such cells can instead be dispensed in the wells of the testing device by the end user just prior to conducting the assay. The kit may further include a set of instructions for using the kit to conduct the intended assay for determining the presence and/or level of a molecule that activates the signal transduction activity in a sample.

When the cells of the cell line according to the present invention are used as a reagent in a kit, the cells are preferably treated with an anti-mitotic and pro-apoptotic agent and stored frozen for future use in a gene-reporter assay as part of a kit. Preparation of cells in this manner is disclosed in US2004-0235157, which is incorporated herein entirely by reference.

The present invention further provides an assay method for determining the presence and/or the level in a sample, by reference to a standard included in the assay, of an extracellular signal that activates the signal transduction activity of a cell surface molecule or complex, preferably a cell surface receptor or complex. This assay method uses cells of the cell line of the present invention. After incubation with a sample in which the presence and/or the level of an extracellular signal that activates the signal transduction activity of a cell surface molecule or complex is sought to be determined, the level of expression of a reporter gene product, encoded in the reporter gene construct carried by the cells of the cell line of the present invention, is determined in the sample. This level of expression as determined by the method according to the present invention is used to then qualitatively determine the presence and/or quantitatively determine the level in a sample of the extracellular signal that activates the signal transduction activity of a cell surface molecule or complex.

It will be appreciated by those of skill in the art that the kit and assay method according to the present can be used either to quantify an agonist or indirectly assay for the level of a molecule that either binds to the extracellular signal molecule as an antagonist or that binds to the antagonist of the extracellular signal molecule. A preferred example of such an indirect assay is where the extracellular signal molecule is TNFα and the molecule that is indirectly assayed through a determination of the level of TNFα is either a TNFα antagonist or a neutralizing antibody against the TNFα antagonist. This embodiment is further described at the end of this section.

Gene reporter assays for Type II interferon and for TNFα are the most preferred embodiments of the present invention. The reporter gene product is preferably firefly luciferase, jellyfish aequorin, or enhanced green fluorescent protein (EGFP) and is preferably under the control of a Type II interferon sensitive chimeric promoter containing GAS from IRF-1 and a minimal SV40 promoter. Examples of such reporter gene constructs in gene reporter assays for IFNγ and TNFα are presented, respectively, in SEQ ID NO:4 and in FIG. 4 (SEQ ID NO:5). SEQ ID NO:4 is the complete sequence of a luciferase gene reporter construct, where the GAS from IRF-1 (nucleotides 41-83 of SEQ ID NO:4) is cloned into the XhoI/BglII site on the pGL2-promoter DNA plasmid (Catalog no. E1631, Promega, Madison, Wis.) immediately upstream of to the SV40 minimal promoter operatively linked to the coding sequence of the firefly luciferase reporter gene. FIG. 4 is a schematic representation of a gene reporter construct in which a 5× tandem repeat of the NFκB recognition/binding site (nucleotides 41-111 of SEQ ID NO:5) is positioned immediately upstream of the SV40 minimal promoter operatively linked to the coding sequence of the firefly luciferase reporter gene (i.e., into the XhoI/BglII cloning site on the pGL2-promoter DNA plasmid). SEQ ID NO:5 is the complete sequence of the resulting plasmid.

As for the cell line of the present invention used in the gene-reporter assay, the cell line is preferably a mammalian or avian cell line, more preferably a human cell line, and most preferably a human promonocytic cell or T-cell (i.e., Jurkatt). Other preferred cell lines include, but are not limited to, human myeloid (i.e., U266R) and human breast adenocarcinoma (i.e., MCF7) cell lines and mouse lymphoma and mouse erythroid leukemia cell lines.

A further application of the gene-reporter assay of the present invention is to use the level of the extracellular signal of interest to indirectly determine the level of an antagonist to the extracellular signal of interest or the level of an antibody (i.e., neutralizing antibody) against the antagonist.

TNFα antagonists are used widely for the treatment of a number of inflammatory disorders including Crohn's disease and rheumatoid arthritis (RA) (Targan et al., 1997; and Lipsky et al., 2000). Repeated treatment with TNFα antagonists elicits the production of antibodies to the antagonist (antibody or recombinant fusion protein) in a number of patients (Baert et al., 2003). Appearance of antibodies to TNFα antagonists is associated with both reduced pharmacodynamics and an impaired clinical response (Baert et al., 2003). Thus, in one study 45% of patients with Crohn's disease treated with Infliximab, a chimeric monoclonal IgG1 antibody against TNFα, developed antibodies against infliximab after the first infusion and 61% after the fifth infusion. Appearance of antibodies to infliximab was associated with an increased risk of infusion reactions and with a shorter duration of clinical response (Baert et al., 2003). Currently TNFα, or antibodies to TNFα are quantified using antibody based assays such as ELISAs (Enzyme Linked Immuno-Sorbent Assay). Such assays can not distinguish between binding antibodies (BAbs) and neutralizing antibodies (NAbs). Although both types of antibodies can negatively impact drug pharmacodynamics, only NAbs can neutralize the biological activity of TNFα antagonists resulting in reduced clinical response and disease progression. Treatment of JUT-4 cells, a cell line according to the present invention developed for use in a gene-reporter assay for TNFα, with an anti-mitotic drug allows cells to be stored frozen for several months without loss of TNFα sensitivity or the need for cell culture (see US2004-0235157 for preparation of cells with an anti-mitotic drug for storage as frozen cells). This assay forms the basis of a method for the selective quantification of neutralizing antibodies to TNFα antagonists including Infliximab (chimeric IgG1), Adlimumab (human IgG1), and Etanercept (human TNFRp75-IgG1Fc fusion protein). Briefly, an amount of TNFα antagonist sufficient to neutralize 10 ng/ml of TNFα is pre-incubated with 10 ng/ml of TNFα and then incubated with serial dilutions of human serum containing antibodies to the TNFα antagonist. The neutralizing titer of the anti-TNFα antagonist antiserum is then estimated from the reciprocal of the serum dilution that results in the detection of 1.0 ng/ml of TNF-α using the JUT-4 gene-reporter assay, following incubation of the serum with 10 ng neutralizing units of the TNFα antagonist and 10 ng/ml of TNFα.

Having now generally described the invention, the same will be more readily understood through reference to the following examples which are provided by way of illustration and are not intended to be limiting of the present invention.

EXAMPLE 1

Human Interferon Gamma Assay

The human pro-monocytic cell line U266R, which lacks a functional Type I IFN receptor (Abramovich et al., 1994) and was derived from human lymphoblastoid cell line U266 (ATCC No. TIB-196), was co-transfected with the Gas-Luc (luciferase) plasmid and a PSV2 neo gene construct, and G418 resistant clones were selected using standard techniques. The Gas-Luc plasmid containing the GAS (IFN Gamma Activated Sequence) sequence from the IRF-1 (Interferon Regulatory Factor 1) gene (GenBank accession number L05078.1 GI:186551; Harada et al., 1989) and a SV40 minimal promoter regulating the transcription of the firefly luciferase reporter gene was constructed by cloning the synthetic double-stranded oligonucleotide tctacaacagcctgatttc-cccg aaatgacggcacgcagccg (SEQ ID NO:1), corresponding to the GAS sequence from the IRF1 gene, in the XhoI/BglII site of the pGL2-promoter vector (Promega). A stable clone, Clone 2, was then selected on the basis of the maximum increase in relative luciferase units (RLU) in response to treatment with human IFNγ relative to untreated control cells. This stable clone of GAS-Luc transfected U266R cells, designated UIG2, was isolated and cultivated in RPMI 1640 medium with 10% fetal bovine serum (FBS) and gentamycin. Cells were seeded at a density of $2 \times 10^5$ cells/ml in RPMI 1640 medium with 10% FBS and then split 1:4 five days later when the cell concentration had attained $0.8 \times 10^6$ cells/ml.

The results of a human interferon gamma (IFNγ) assay in a human U937 cell line, which has functional Type I and Type II IFN receptors and which has been co-transfected with the Gas-Luc plasmid and the PSV2 neo gene construct, are shown in Table 1 below.

TABLE 1

| RLU (Relative Luciferase Units): Fold Increase | |
|---|---|
| IFNγ (IU/ml) | |
| 10.0 | 1.25 |
| 100 0 | 1.50 |
| IFNα (IU/ml) | |
| 1.0 | 1.5 |
| 100.0 | 3.0 |

The increase in RLU in response to human IFNγ was minimal relative to untreated control cells, and it can be seen that the specificity for IFNγ was poor as treatment of cells with human IFNα exhibited a relatively large increase in RLU.

By contrast, the results of the human IFNγ assay in stable Clone 2 of the human U266R cell line, which lacks a functional Type I IFN receptor, and was transfected with the same gene-reporter construct as used to transfect U937 cells, are shown in Table 2 below.

TABLE 2

| RLU (Relative Luciferase Units): Fold Increase | |
|---|---|
| IFNγ (IU/ml) | |
| 1.0 | 1.5 |
| 100 0 | 9 |
| IFNα (IU/ml) | |
| 100.0 | <0.15 |

These results show that the increase in RLU in response to human IFNγ was large relative to untreated control cells, and it can be seen that the specificity for IFNγ was good as treatment of cells with human IFNα did not give a significant increase in RLU.

EXAMPLE 2

Human TNF-α Assay

A gene-reporter assay is established here for the quantification of TNFα using a cell line transfected with a gene-reporter construct such that the ensemble is capable of detecting and responding to low levels of TNFα in a highly specific manner.

In an initial series of experiments, the promoter region (−500 to +1 nucleotide) of the IRF-1 gene (GenBank accession number L05078.1 GI:186551; Harada et al., 19389) was cloned upstream of a SV40 minimal promoter in the XhoI/BglII site of the pGL2-promoter DNA vector (Promega) in order to regulate the transcription of the firefly luciferase reporter-gene (FIG. 1). Human pro-monocytic U927 cells were then co-transfected with the IRF-Luc plasmid and a PSV2 neo gene construct and G418 resistant clones were selected using standard techniques. A stable clone, Clone 2, was then selected on the basis of the maximum increase in relative luciferase units (RLU) in response to treatment with human TNFα relative to untreated control cells. The human T-cell line Jurkat, which is refractory to IL-2 and poorly responsive to IFNγ, was co-transfected with the 5×NFκB-Luc plasmid and a PSV2 neo gene construct, and G418 resistant clones were selected using standard techniques. The 5×NFκB-Luc plasmid containing a 5 times tandem repeat of the canonical NFkB recognition sequence and a SV40 minimal promoter regulating the transcription of the firefly luciferase reporter gene was constructed by cloning the synthetic double-stranded oligonucleotide (FIG. 4), corresponding to the 5× tandem repeat of the canonical NFκB recognition sequence, into the XhoI/BglII site of the pGL2-promoter vector (Promega). A stable clone, Clone 4, was then selected on the basis of the maximum increase in relative luciferase units (RLU) in response of treatment with human TNFα relative to untreated control cells.

A stable clone, Clone 4, of 5×NFκB-Luc transfected Jurkat cells, designated JUT-4, was isolated and cultivated in RPMI 1640 medium with 10% fetal bovine serum (FBS) and gentamycin. Cells were seeded at a density $1 \times 10^5$ cells/ml in RPMI 1640 medium with 10% FBS and then split 1:10 five days later when the cell concentration had attained $1.0 \times 10^6$ cells/ml.

TABLE 3

| Human MCF7 Cells transfected with the IRF-1 promoter, Clone #1 | |
|---|---|
| RLU (Relative Luciferase Units): Fold Increase | |
| TNFα (ng/ml) | |
| 0.1 | 0* |
| 100.0 | 0* |
| IL2 (ng/ml) | |
| 1.0 | <0.1 |
| 100.0 | <0.1 |

*Complete absence of a RLU response due to the induction of massive apoptosis in the assay cells MCF-7 cells transfected with the IRF-1 promoter are highly sensitive to TNFα but are unsuitable as the basis for a gene-reporter assay for TNFα due to the induction of massive apoptosis in the assay cells and rapid cell death.

U937 Cells, Clone #2

Figure 3:
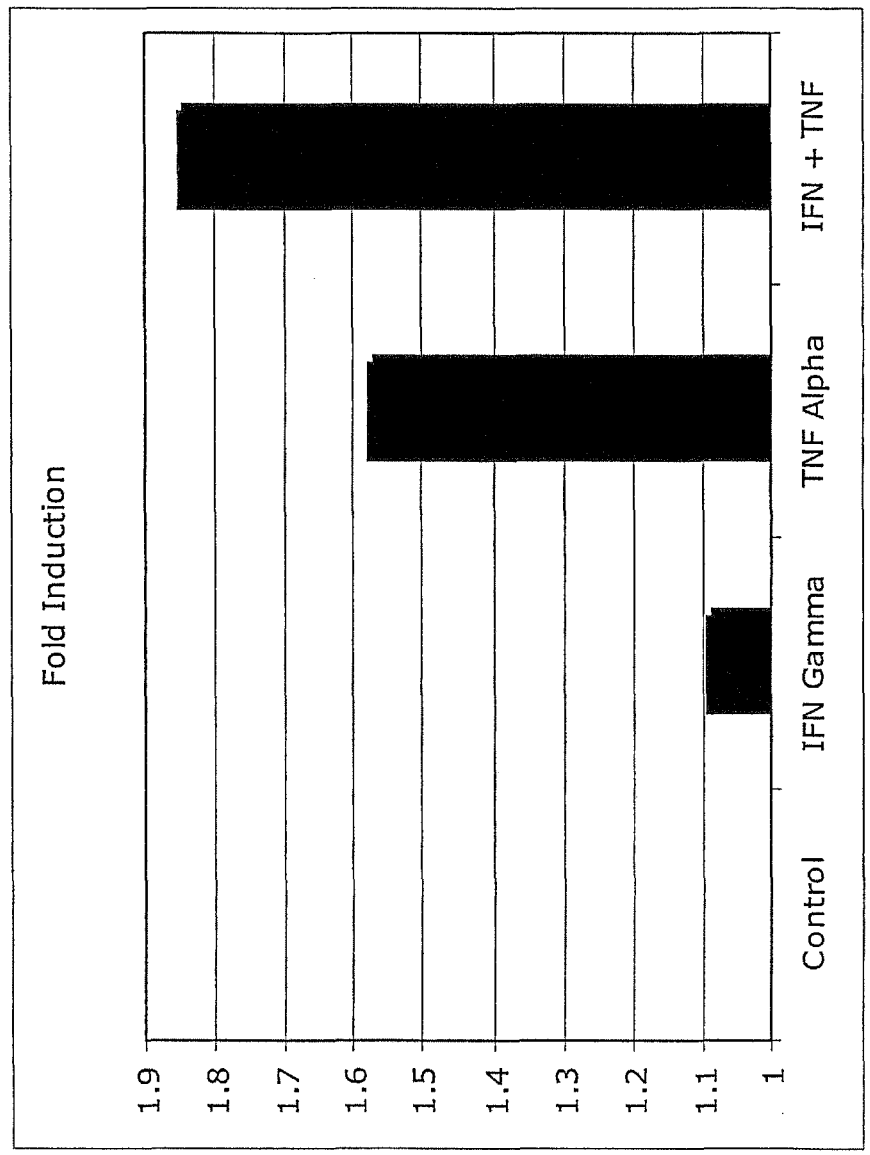
FIG. 3 is a graph showing the x-fold induction of firefly luciferase activity as converted from the data shown in FIG. 2.

Treatment of IRF-Luc2 cells transfected with the IRF-Luc plasmid with TNFα (10 ng) resulted in a modest 1.58 fold increase in RLU, while treatment of IRF-Luc2 cells with IFNγ or TNFα+IFNγ gave a 1.1 and 1.85 fold increase in RLU respectively (FIG. 3).

Jurkat Cells, Clone #4

TABLE 4

| RLU (Relative Luciferase Units): Fold Increase | |
|---|---|
| TNFα (ng/ml) | |
| 0.1 | 2.0 |
| 100.0 | 10.0 |
| IFNγ (IU/ml) | |
| 100.0 | <0.10 |
| IL-2 (ng/ml) | |
| 1.0 | <0.10 |
| 100 | <0.15 |

Jurkat, JUT-4, cells transfected with the 5×NFκB promoter are highly sensitive to TNFα and completely unresponsive to either IFNγ or IL-2 and therefore provide an ideal basis for a gene-reporter assay capable of detecting and quantifying low levels of TNFα in a highly specific manner.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Abramovich et al. (1994) Differential tyrosine phosphorylation of the IFNAR chain of the type I interferon receptor and of an associated surface protein in response to IFN-alpha and IFN-beta. *Embo J.* 13:5871.

Ank et al JICR 2006, 26:373-379

Alton et al. (1979) Nucleotide sequence analysis of the chloramphenicol resistance transposon Tn9. *Nature* 282: 864

Baert et al., *N Engl J Med* 2003, 348:601-08

Baldwin et al. (1984) Cloning of the luciferase structural genes from *Vibrio harveyi* and expression of bioluminescence in *Escherichia coli. Biochemistry* 23:3663-3667

Balog et al., *Pathobiology* 2004; 71(5):274-280

Barbieri et al. (1994) Activation of the protein tyrosine kinase tyk2 by interferon alpha/beta. *Eur J. Biochem.* 223:427.

Basu et al. (1998) The antiviral action of interferon is potentiated by removal of the conserved IRTAM domain of the IFNAR1 chain of the interferon alpha/beta receptor: effects on JAK-STAT activation and receptor down-regulation. *Virology.* 242:14.

Bazan, (1990). Structural design and molecular evolution of a cytokine receptor superfamily. *Proc Natl Acad Sci USA.* 87:6934.

Bouche et al. (1987) Basic fibroblast growth factor enters the nucleolus and stimulates the transcription of ribosomal genes in ABAE cells undergoing G0 - - - G1 transition. *Proc. Natl. Acad. Sci. U.S.A.* 84:6770-6774

Boulter et al. (1986) Isolation of a cDNA clone coding for a possible neural nicotinic acetylcholine receptor alpha-subunit. *Nature* 319:368-374

Boulter et al. (1990) Alpha 3, alpha 5, and beta 4: three members of the rat neuronal nicotinic acetylcholine receptor-related gene family form a gene cluster. *J. Biol. Chem.* 265:4472

Boyanova et al, *Analytical Biochemistry,* 2002; 308:178-181

Branca et al. (1981) Evidence that types I and II interferons have different receptors. *Nature.* 294:768.

Bunzow et al. (1988) Cloning and expression of a rat D2 dopamine receptor cDNA. *Nature* 336:783-787

Canosi et al. (1996) A highly precise reporter gene bioassay for type I interferon. *Journal of Immunological Methods* 199:69

Changelian et al. (1989) Structure of the NGFI-A gene and detection of upstream sequences responsible for its transcriptional induction by nerve growth factor. *Proc. Natl. Acad. Sci. USA* 86:377-381

Changelian et al. (1989) Structure of the NGFI-A gene and detection of upstream sequences responsible for its transcriptional induction by nerve growth factor. *Proc. Natl. Acad. Sci.* 86:377-381

Cleary et al. (1994) Knockout and reconstitution of a functional human type I interferon receptor complex. *Journal of Biological Chemistry.* 269:18747.

Cohen et al. (1995) Ligand-induced association of the type I interferon receptor components. *Mol Cell Biol.* 15:4208.

Colamonici et al. (1994) Direct binding to and tyrosine phosphorylation of the alpha subunit of the type I interferon receptor by p135tyk2 tyrosine kinase. *Mol. Cell. Biol.* 14:8133.

Comb et al. (1986) *Nature* 323:353-356

Constantinescu et al. (1994) Role of interferon alpha/beta receptor chain 1 in the structure and transmembrane signaling of the interferon alpha/beta receptor complex. *Proc Natl Acad Sci USA.* 91:9602.

Constantinescu et al. (1995) Expression and signaling specificity of the IFNAR chain of the type I interferon receptor complex. *Proc Natl Acad Sci USA.* 92:10487.

Cook et al. (1996) Differential responsiveness of a splice variant of the human type I interferon receptor to interferons. *J Biol. Chem.* 271:13448.

Cowin et al., *Wound Repair Regen.* 2006; 14(4):421-426

Cutrone et al. (1997) Contributions of cloned type I interferon receptor subunits to differential ligand binding. *FEBS Lett.* 404:197.

Darnell et al. (1994) Jak-STAT pathways and transcriptional activation in response to IFNs and other extracellular signaling proteins. *Science.* 264:1415.

De Maeyer et al. (1988) Interferons and other regulatory cytokines. *John Wiley, New york:*69.

Deneris et al. (1988) Primary structure and expression of beta 2: a novel subunit of neuronal nicotinic acetylcholine receptors. *Neuron* 1:45-54

Deneris et al. (1989) Beta 3: a new member of nicotinic acetylcholine receptor gene family is expressed in brain. *J. Biol. Chem.* 264: 6268-6272 deWet et al. (1987) Firefly luciferase gene: structure and expression in mammalian cells. *Mol. Cell. Biol.* 7:725-737

Diaz et al. (1993) Nomenclature of the human interferon genes. *J Interferon Res.* 13:443.

Diebold S S, Kaisho T, Hemmi H, Akira S, Reis, E., and Sousa C. (2003). Innate antiviral responses by means of TLR7-mediated recognition of single-stranded RNA. *Science.* 303, 1529-1531.

Dixon et al. (1986) Cloning of the gene and cDNA for mammalian beta-adrenergic receptor and homology with rhodopsin. *Nature* 321:75-79

Domanski et al. (1995) Cloning and expression of a long form of the beta subunit of the interferon alpha beta receptor that is required for signaling. *J Biol. Chem.* 270:21606.

Domanski et al. (1996) The type-I interferon receptor. The long and short of it. *Cytokine Growth Factor Rev.* 7:143.

Duvoisin et al. (1989) The functional diversity of the neuronal nicotinic acetylcholine receptors is increased by a novel subunit: beta 4. *Neuron* 3:487-496

Ellis et al. (1988) Sequence and expression of mRNAs encoding the alpha 1 and alpha 2 subunits of a DHP-sensitive calcium channel. *Science* 241:1661-1664

Engebrecht et al. (1984) Identification of genes and gene products necessary for bacterial bioluminescence. *PNAS* 1:4154-4158

Fiette et al. (1995) Theiler's virus infection of 129Sv mice that lack the interferon alpha/beta or interferon gamma receptors. *Journal of Experimental Medicine.* 181:2069.

Fink et al. (1988), The CGTCA sequence motif is essential for biological activity of the vasoactive intestinal peptide gene cAMP-regulated enhancer. *Proc. Natl. Acad. Sci.* 85:6662-6666

Frielle et al. (1987) Cloning of the cDNA for the human beta 1-adrenergic receptor. *Proc. Natl. Acad. Sci.* 84:7920-7924

Fu, (1992) A transcription factor with SH2 and SH3 domains is directly activated by an interferon alpha-induced cytoplasmic protein tyrosine kinase(s). *Cell.* 70:323.

Goldman et al. (1987) Members of a nicotinic acetylcholine receptor gene family are expressed in different regions of the mammalian central nervous system. *Cell* 48:965-973

Hall et al. (1983) *J. Mol. Appl. Gen.* 2:101

Hammerling et al. (1998) The β-gal interferon assay: a new, precise, and sensitive method. *Journal of Interferon and Cytokine Research* 18:451-460

Harada et al, Cell, 1989, 58:729-739

Heil F, Hemmi H, Hochrein H, Ampenberger F, Kirschning C, Akira S, Lipford G, Wagner H, and Bauer S. (2003). Species-specific recognition of single-stranded RNA via toll-like receptor 7 and 8. *Science,* 303, 1526-1529.

Hemmi, H., Takeuchi, O., Sato, S., Yamamoto, M., Kaisho, T., Santon H., Kawai, T., Hoshino, K., Takeda, K, and Akira, S. (2004). The roles of two ikappaB kinases in lipopolysaccharide and double stranded RNA signaling and viral infection. *J. Exp. Med.* 199, 1641-1650.

Hemmi, H., Takeuchi, O., Kawai, T., Kaisho, T., Sato, S., Sanjo, H., Matsumoto, M., Hoshino, K., Wagner, H., Takeda, K., and Akira, S. (2000). A Toll-like receptor recognizes bacterial DNA. *Nature,* 408, 740-745.

Hollmann et al. (1989) Cloning by functional expression of a member of the glutamate receptor family. *Nature* 342:643-648

Horvath et al. (1995) A STAT protein domain that determines DNA sequence recognition suggests a novel DNA-binding domain Genes Dev. 9:984-994

Hwang et al. (1995) A null mutation in the gene encoding a type I interferon receptor component eliminates antiproliferative and antiviral responses to interferons alpha and beta and alters macrophage responses. *Proc Natl Acad Sci USA.* 92:11284.

Ihle, (1995) Cytokine receptor signalling. *Nature.* 377:591.

Imanishi et al., *J. Immunol,* 2000, 165:3907-16

Jay et al. (1990) Primary structure of the gamma subunit of the DHP-sensitive calcium channel from skeletal muscle. *Science* 248:490-492

Johnson et al. (1986) *Cell* 47:545-554

Julius et al. (1988) Molecular characterization of a functional cDNA encoding the serotonin 1c receptor. *Science* 241: 558-564

Julius et al. (1990) The 5HT2 receptor defines a family of structurally distinct but functionally conserved serotonin receptors. *PNAS* 87:928-932

Kayano et al, (1988) Primary structure of rat brain sodium channel III deduced from the cDNA sequence. *FEBS Lett.* 228:187-194

King, D. P., Jones, P. P., *J. Immunol. Methods,* 1983, 131:315-320

Kobilka et al. (1987) An intronless gene encoding a potential member of the family of receptors coupled to guanine nucleotide regulatory proteins. *Nature* 329:75-79

Kobilka et al. (1987) Cloning, sequencing, and expression of the gene coding for the human platelet alpha 2-adrenergic receptor. *Science* 238:650-656

Lallemand et al. (1996) Constitutive expression of specific interferon isotypes in peripheral blood leukocytes from normal individuals and in promonocytic U937 cells. *J Leukoc Biol.* 60:137-46

Langer et al. (1996) Interferon receptors. *Biotherapy.* 8:163

Levitan et al. (1988) Structural and functional basis for GABAA receptor heterogeneity. *Nature* 335:76-79

Levy et al. (1988) Interferon-induced nuclear factors that bind a shared promoter element correlate with positive and negative control-Genes Dev. 2:383-393

Lewis, (1995) A sensitive biological assay for interferons. *Journal of Immunological Methods* 185:9-17

Lim et al. (1993) Cloning and characterization of a bovine alpha interferon receptor. *Biochim Biophys Acta.* 1173: 314.

Lipsky et al., *N Engl J Med* 2000, 343:1594-602

Lleonart et al., (1990) A novel, quantitative bioassay for type I interferon using a recombinant indicator cell line. *Biotechnology* 8:1263-1267

Lutfalla et al. (1992) The structure of the human interferon alpha/beta receptor gene. *J Biol. Chem.* 267:2802.

Lutfalla et al. (1995) Mutant U5A cells are complemented by an interferon-alpha beta receptor subunit generated by alternative processing of a new member of a cytokine receptor gene cluster. *Embo J.* 14:5100.

Malu et al, *J. Immunol. Methods,* 2003; 272:55-65

Marotte et al, *Arthritis Res. Ther.* 2005; 7(1):R149-155

McFarlane et al, *FEBS Letters,* 2002, 515:119-126

McKinnon, D. (1989) Isolation of a cDNA clone coding for a putative second potassium channel indicates the existence of a gene family. *J. Biol. Chem.* 264:8230-8236

Meager, A. *Methods;* 2006, 38:237-252

Merlin et al. (1985) 125I-labelled human interferons alpha, beta and gamma: comparative receptor-binding data. *J Gen Virol.* 66:1149.

Montminy et al. (1986), Identification of a cyclic-AMP-responsive element within the rat somatostatin gene. *Proc. Natl. Acad. Sci.* 83:6682-6686

Mouchel-Vielh et al. (1992). Specific antiviral activities of the human alpha interferons are determined at the level of receptor (IFNAR) structure. *FEBS Lett.* 313:255.

Muller et al. (1994) Functional role of type I and type II interferons in antiviral defense. *Science.* 264:1918.

Noda et al. (1986) Nature 320:188-192

Novick et al. (1994) The human interferon alpha/beta receptor: characterization and molecular cloning. *Cell.* 77:391.

Perry et al., (1999) Cloning of interferon-stimulated gene 17: The promoter and nuclear proteins that regulate transcription. *Molecular Endocrinology,* 13:1197-1206

Perry, A. K., Chow, E. K., Goodnougy, J. B., Yeh, W. C., and Cheng, G. (2004). Differential requirement for TANK-binding kinase-1 in type I interferon responses Pestka et al. (1987) Interferons and their actions. *A. Rev. Biochem.* 56:727.

Platanias et al. (1994) Tyrosine phosphorylation of the alpha and beta subunits of the type I interferon receptor. Interferon-beta selectively induces tyrosine phosphorylation of an alpha subunit-associated protein. *J. Biol. Chem.* 269: 17761.

Pritchett et al. (1989) Importance of a novel GABAA receptor subunit for benzodiazepine pharmacology. *Nature* 338:582-585

Rider et al. (2003) A B cell-based sensor for rapid identification of pathogens. *Science* 301:213-215

Russell-Harde et al. (1995) Reconstitution of a high affinity binding site for type I interferons. *J Biol. Chem.* 270: 26033.

Ruth et al. (1989) Primary structure of the beta subunit of the DHP-sensitive calcium channel from skeletal muscle. *Science* 245:1115-1118

Sato et al., (2006) *J Immunol* 176(12):7686-94

Schindler et al. (1992) Interferon-dependent tyrosine phosphorylation of a latent cytoplasmic transcription factor [see comments]. *Science.* 257:809.

Schofield et al. (1987) Sequence and functional expression of the GABA A receptor shows a ligand-gated receptor superfamily. *Nature* 328:221-227

Schumacher et al. (1994) The chicken Mx promoter contains an ISRE motif and confers interferon inducibility to a reporter gene in chick and monkey cells. *Virology* 15:203 (1):144-8

Schwamborn et al., *BMC Genomics* 2003, 4:46-58

Sheppard et al *Nat. Immunol.* 2003; 4:63-68

Sheng et al. (1990) The regulation and function of c-fos and other immediate early genes in the nervous system. *Neuron* 4:477-485

Shivers, B. D. (1989) *Neuron* 3:327-337

Short et al. (1986) *J. Biol. Chem.* 261:9721-9726

Steinhoff et al. (1995) Antiviral protection by vesicular stomatitis virus-specific antibodies in alpha/beta interferon receptor-deficient mice. *Journal of Virology.* 69:2153.

Steinman, R. M., and Hemmi, H. (2006). Dendritic cells: translating innate to adaptive immunity. *Curr. Top. Microbiol. Immunol.* 311, 17-58.

Stormann et al. (1990) Molecular cloning and expression of a dopamine D2 receptor from human retina. *Molec. Pharm.* 37:1-6

Tanabe et al. (1987) Primary structure of the receptor for calcium channel blockers from skeletal muscle. *Nature* 328:313-E318

Taniguchi, (1995) Cytokine signaling through nonreceptor protein tyrosine kinases. *Science.* 268:251.

Targan et al., *N Engl J Med* 1997, 337:1029-35

Tempel et al. (1988) Cloning of a probable potassium channel gene from mouse brain. *Nature* 332:837-839

Thoreau et al. (1991) Structural symmetry of the extracellular domain of the cytokine/growth hormone/prolactin receptor family and interferon receptors revealed by hydrophobic cluster analysis. *FEBS Lett.* 282:26.

Toh et al. (1989) Isolation and characterization of a rat liver alkaline phosphatase gene. A single gene with two promoters. *Eur. J. Biochem.* 182:231-238

Uddin et al. (1995) Interaction of the transcriptional activator Stat-2 with the type I interferon receptor. *J Biol. Chem.* 270:24627.

Uematsu, S., and Akira, S. (2007). Toll-like receptors and type I interferons. *J. Biol. Chem.* 282, 15319-15323.

Uze et al. (1990) Genetic transfer of a functional human interferon alpha receptor into mouse cells: cloning and expression of its cDNA. *Cell.* 60:225.

Uze et al. (1992) Behavior of a cloned murine interferon alpha/beta receptor expressed in homospecific or heterospecific background. *Proc Natl Acad Sci USA.* 89:4774.

Uzé et al. (1995) Alpha and beta interferons and their receptor and their friends and relations. *Journal of Interferon & Cytokine Research.* 15:3.

van den Broek et al. (1995) Antiviral defense in mice lacking both alpha/beta and gamma interferon receptors. *Journal of Virology.* 69:4792.

Vandenbroek et al. (1995) Immune defense in mice lacking type I and/or type II interferon receptors. *Immunol Rev.* 148:5.

Velazquez et al. (1995) Distinct domains of the protein tyrosine kinase tyk2 required for binding of interferon-alpha/beta and for signal transduction. *J Biol. Chem.* 270: 3327.

Wada et al. (1988) Functional expression of a new pharmacological subtype of brain nicotinic acetylcholine receptor. *Science* 240:330-334

Yan et al. (1996) Molecular characterization of an alpha interferon receptor 1 subunit (IFNaR1) domain required for TYK2 binding and signal transduction. *Mol Cell Biol.* 16:2074.

Yan et al. (1996) Phosphorylated interferon-alpha receptor 1 subunit (IFNaR1) acts as a docking site for the latent form of the 113 kDa STAT2 protein. *EMBO J.* 15:1064.

Yeh et al. (1987) Ultrastructural localization of a platelet-derived growth factor/v-sis-related protein(s) in cytoplasm and nucleus of simian sarcoma virus-transformed cells. *Proc. Natl. Acad. Sci. U.S.A.* 84:2317-2321

Ymer et al. (1989) GABAA receptor beta subunit heterogeneity: functional expression of cloned cDNAs. *EMBO J.* 8:1665-1670

Yoneyama, M., Fujita, T. (2007). Function of RIG-1-like receptors in antiviral innate immunity. J. Biol. Chem. 282, 15315-15318.

Zlokarnik et al. (1998) Quantitation of transcription and clonal selection of single living cells with β-lactamase as reporter. *Science* 279:84-88.

What is claimed is:

1. In a cell line stably transformed with a reporter gene construct comprising a nucleotide sequence encoding a reporter gene product operatively linked to a transcriptional control element that is activated as part of the NFκB signal transduction pathway activated by an interaction of a first extracellular signal with a first cell surface molecule or complex, wherein the transcriptional control element is one that bound by NFκB so as to activate said transcriptional control element and thereby induce or upregulate transcription of the reporter gene, the improvement whereby the sensitivity and/or the specificity of the response of the cell line to the extracellular signal is improved, wherein:
   a) said transcriptional control element is a synthetic promoter consisting of a minimal promoter and a regulatory sequence, said minimal promoter being regulated by said regulatory sequence, said regulatory sequence consisting of a plurality of response elements specific for NFκB; and
   b) the cells of said cell line lack at least one functional second cell surface molecule or complex that, if present on the cell line, would interact with a second extracellular signal that is one of the principal signals known to activate the NFκB signal transduction pathway though said second cell surface molecule or complex, thereby modulating the transcription of the reporter gene and causing interference with the first extracellular signal when the cell line is used in a gene reporter assay.

2. The cell line of claim 1, wherein said regulatory sequence consists of a synthetic nucleotide sequence that consists of a tandem repeat of the naturally occurring or consensus sequence of the binding site for NFκb.

3. The cell line of claim 2, wherein said regulatory sequence consists of the sequence of SEQ ID NO:2.

4. The cell line of claim 1, wherein said first extracellular signal is tumor necrosis factor-α (TNFα).

5. The cell line of claim 1, wherein the cells of said cell line have been genetically engineered to knock out at least one functional second cell surface molecule or complex.

6. The cell line of claim 1, wherein at least the extracellular portion of said first cell surface molecule or complex is that of a first animal species and the cells of said cell line are cells of a second animal species that have been genetically engineered to knock in said first cell surface molecule or complex.

7. The cell line of claim 1, wherein said first cell surface molecule or complex is a cell surface receptor.

8. The cell line of claim 1 in a frozen state, wherein said cell line has the property that it will maintain signal transduction activity of the NFκB signal transduction pathway activated by interaction of said first extracellular signal with said first cell surface molecule or complex for at least one hour after being thawed but will lose said signal transduction activity and undergo cellular death in no more than about 30 days at a temperature above freezing after being thawed.

9. The cell line of claim 1, wherein said first extracellular signal is TNFα and said first cell surface molecule or complex is TNFα receptor.

10. The cell line according to claim 1, wherein the cells of said cell line have been engineered to knock down said at least one functional second cell surface molecule or complex.

11. The cell line of claim 1, wherein said principal signals known to activate the NFκB signal transduction pathway are selected from the group consisting of TNFα, IL-6, IL-2, IL-5, and IFN-γ.

12. A kit for determining the presence and/or level in a sample of TNFα, comprising:
   a testing device having a plurality of wells; and
   a reagent containing a plurality of cells of the cell line of claim 9.

13. The kit of claim 12, wherein said testing device is a microtiter plate.

14. The kit of claim 12, wherein said reagent is disposed in the wells of said testing device.

15. A method for determining the level in a sample of an extracellular signal that activates the NFκB signal transduction pathway by interaction of the extracellular signal with a cell surface molecule or complex, comprising:
   incubating cells of the cell line of claim 1 with a sample in which the level of an extracellular signal that activates the signal transduction activity of a cell surface molecule is sought to be determined; and
   determining the level of expression of the reporter gene product in the cells to thereby determine the level in the sample of the extracellular signal that activates the signal transduction activity of the cell surface molecule or complex.

16. The method of claim 15, wherein the cell surface molecule is a TNFα receptor and the extracellular signal is TNFα.

17. The method of claim 15, wherein determining the level in a sample of TNFα indirectly determines the level of a TNFα antagonist or the level of an antibody against the TNFα antagonist.

18. In a cell line stably transformed with a reporter gene construct comprising a nucleotide sequence encoding a reporter gene product operatively linked to a transcriptional control element that is activated as part of the signal transduction pathway activated by an interaction of a Type II interferon with a first cell surface molecule or complex, wherein the transcriptional control element is one that is bound by STAT1-STAT1 homodimer so as to activate said transcriptional control element and thereby induce or upregulate transcription of the reporter gene, the improvement whereby the sensitivity and/or the specificity of the response of the cell line to the extracellular signal is improved, wherein:
   a) said transcriptional control element is a synthetic promoter consisting of a minimal promoter and a regulatory sequence, said minimal promoter being regulated by said regulatory sequence, said regulatory sequence consisting of a gamma activated sequence (GAS); and b) the cells of said cell line lack a functional Type I interferon receptor that, if present on the cell line, would interact with a Type I interferon and cause interference with the Type II interferon when the cell line is used in a gene reporter assay.

19. The cell line of claim 18, wherein the GAS sequence is SEQ ID NO:3.

20. The cell line of claim 18, wherein the GAS sequence is from IRF-1.

21. The cell line of claim 18, wherein the GAS sequence is nucleotides 41-83 of SEQ ID NO:4.

22. The cell line of claim 18 in a frozen state, wherein said cell line has the property that it will maintain signal transduction activity activated by interaction of a Type II interferon with said first cell surface molecule or complex for at least one hour after being thawed but will lose said signal transduction activity and undergo cellular death in no more than about 30 days at a temperature above freezing after being thawed.

23. The cell line of claim 18, wherein said Type I interferon receptor has been genetically knocked out.

24. A kit for determining the presence and/or level in a sample of IFNγ, comprising:
 a testing device having a plurality of wells; and
 a reagent containing a plurality of cells of the cell line of claim 18.

25. The kit of claim 24, wherein said testing device is a microtiter plate.

26. The kit of claim 24, wherein said reagent is disposed in the wells of said testing device.

27. A method for determining the level in a sample of IFNγ that activates the signal transduction pathway from a Type II interferon receptor, comprising:
 incubating cells of the cell line of claim 18 with a sample in which the level of IFNγ is sought to be determined; and
 determining the level of expression of the reporter gene product in the cells to thereby determine the level in the sample of IFNγ.

\* \* \* \* \*

SEQUENCE LISTING

```
<160> NUMBER OF SEQ ID NOS: 5

<210> SEQ ID NO 1
<211> LENGTH: 42
<212> TYPE: DNA
<213> ORGANISM: Artificial
<220> FEATURE:
<223> OTHER INFORMATION: synthetic

<400> SEQUENCE: 1
tctacaacag cctgatttcc ccgaaatgac ggcacgcagc cg                          42

<210> SEQ ID NO 2
<211> LENGTH: 70
<212> TYPE: DNA
<213> ORGANISM: Artificial
<220> FEATURE:
<223> OTHER INFORMATION: synthetic

<400> SEQUENCE: 2
tggggacttt ccgctgggga ctttccgctg gggactttcc gctggggact tccgctggg       60 gactttccgc                                                             70

<210> SEQ ID NO 3
<211> LENGTH: 21
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 3
nnnsanttcc gggaantgns n                                                21

<210> SEQ ID NO 4
<211> LENGTH: 5834
```

<212> TYPE: DNA
<213> ORGANISM: Artificial
<220> FEATURE:
<223> OTHER INFORMATION: synthetic

<400> SEQUENCE: 4

| | | | | | |
|---|---|---|---|---|---|
| cccgggaggt | accgagctct | tacgcgtgct | agctcgagtc | tacaacagcc | tgatttcccc | 60 |
| gaaatgacgg | cacgcagccg | agatctgcat | ctcaattagt | cagcaaccat | agtcccgccc | 120 |
| ctaactccgc | ccatcccgcc | cctaactccg | cccagttccg | cccattctcc | gccccatggc | 180 |
| tgactaattt | tttttattta | tgcagaggcc | gaggccgcct | cggcctctga | gctattccag | 240 |
| aagtagtgag | gaggcttttt | tggaggccta | ggcttttgca | aaaagcttgg | cattccggta | 300 |
| ctgttggtaa | aatggaagac | gccaaaaaca | taaagaaagg | cccggcgcca | ttctatcctc | 360 |
| tagaggatgg | aaccgctgga | gagcaactgc | ataaggctat | gaagagatac | gccctggttc | 420 |
| ctggaacaat | tgcttttaca | gatgcacata | tcgaggtgaa | catcacgtac | gcggaatact | 480 |
| tcgaaatgtc | cgttcggttg | gcagaagcta | tgaaacgata | tgggctgaat | acaaatcaca | 540 |
| gaatcgtcgt | atgcagtgaa | aactctcttc | aattctttat | gccggtgttg | ggcgcgttat | 600 |
| ttatcggagt | tgcagttgcg | cccgcgaacg | acatttataa | tgaacgtgaa | ttgctcaaca | 660 |
| gtatgaacat | ttcgcagcct | accgtagtgt | ttgtttccaa | aaaggggttg | caaaaaattt | 720 |
| tgaacgtgca | aaaaaaatta | ccaataatcc | agaaaattat | tatcatggat | tctaaaacgg | 780 |
| attaccaggg | atttcagtcg | atgtacacgt | tcgtcacatc | tcatctacct | cccggtttta | 840 |
| atgaatacga | ttttgtacca | gagtcctttg | atcgtgacaa | acaattgca | ctgataatga | 900 |
| attcctctgg | atctactggg | ttacctaagg | gtgtggccct | tccgcataga | actgcctgcg | 960 |
| tcagattctc | gcatgccaga | gatcctattt | ttggcaatca | aatcattccg | gatactgcga | 1020 |
| ttttaagtgt | tgttccattc | catcacggtt | ttggaatgtt | tactacactc | ggatatttga | 1080 |
| tatgtggatt | tcgagtcgtc | ttaatgtata | gatttgaaga | agagctgttt | ttacgatccc | 1140 |
| ttcaggatta | caaaattcaa | agtgcgttgc | tagtaccaac | cctatttca | ttcttcgcca | 1200 |
| aaagcactct | gattgacaaa | tacgatttat | ctaatttaca | cgaaattgct | tctggggggcg | 1260 |
| cacctctttc | gaaagaagtc | ggggaagcgg | ttgcaaaacg | cttccatctt | ccagggatac | 1320 |
| gacaaggata | tgggctcact | gagactacat | cagctattct | gattacaccc | gagggggatg | 1380 |
| ataaaccggg | cgcggtcggt | aaagttgttc | cattttttga | agcgaaggtt | gtggatctgg | 1440 |
| ataccgggaa | aacgctgggc | gttaatcaga | gaggcgaatt | atgtgtcaga | ggacctatga | 1500 |
| ttatgtccgg | ttatgtaaac | aatccggaag | cgaccaacgc | cttgattgac | aaggatggat | 1560 |
| ggctacattc | tggagacata | gcttactggg | acgaagacga | acacttcttc | atagttgacc | 1620 |
| gcttgaagtc | tttaattaaa | tacaaaggat | atcaggtggc | ccccgctgaa | ttggaatcga | 1680 |
| tattgttaca | acaccccaac | atcttcgacg | cgggcgtggc | aggtcttccc | gacgatgacg | 1740 |
| ccggtgaact | tcccgccgcc | gttgttgttt | tggagcacgg | aaagacgatg | acggaaaaag | 1800 |
| agatcgtgga | ttacgtcgcc | agtcaagtaa | caaccgcgaa | aaagttgcgc | ggaggagttg | 1860 |
| tgtttgtgga | cgaagtaccg | aaaggtctta | ccggaaaact | cgacgcaaga | aaaatcagag | 1920 |
| agatcctcat | aaaggccaag | aagggcggaa | agtccaaatt | gtaaaatgta | actgtattca | 1980 |
| gcgatgacga | aattcttagc | tattgtaata | ctgcgatgag | tggcagggcg | gggcgtaatt | 2040 |
| tttttaaggc | agttattggt | gcccttaaac | gcctggttgc | tacgcctgaa | taagtgataa | 2100 |
| taagcggatg | aatggcagaa | attcgccgga | tctttgtgaa | ggaaccttac | ttctgtggtg | 2160 |
| tgacataatt | ggacaaacta | cctacagaga | tttaaagctc | taaggtaaat | ataaaatttt | 2220 |

```
taagtgtata atgtgttaaa ctactgattc taattgtttg tgtattttag attccaacct   2280
atggaactga tgaatgggag cagtggtgga atgcctttaa tgaggaaaac ctgttttgct   2340
cagaagaaat gccatctagt gatgatgagg ctactgctga ctctcaacat tctactcctc   2400
caaaaaagaa gagaaaggta aagaccccca aggactttcc ttcagaattg ctaagttttt   2460
tgagtcatgc tgtgtttagt aatagaactc ttgcttgctt tgctatttac accacaaagg   2520
aaaaagctgc actgctatac aagaaaatta tggaaaaata ttctgtaacc tttataagta   2580
ggcataacag ttataatcat aacatactgt tttttcttac tccacacagg catagagtgt   2640
ctgctattaa taactatgct caaaaattgt gtacctttag cttttttaatt tgtaaagggg   2700 ttaataagga atatttgatg tatagtgcct tgactagaga tcataatcag ccataccaca   2760
tttgtagagg ttttacttgc tttaaaaaac ctcccacacc tcccccctgaa cctgaaacat   2820 aaaatgaatg caattgttgt tgttaacttg tttattgcag cttataatgg ttacaaataa   2880
agcaatagca tcacaaattt cacaaataaa gcatttttt  cactgcattc tagttgtggt   2940
ttgtccaaac tcatcaatgt atcttatgat gtctggatcc gtcgaccgat gcccttgaga   3000
gccttcaacc cagtcagctc cttccggtgg gcgcggggca tgactatcgt cgccgcactt   3060
atgactgtct tctttatcat gcaactcgta ggacaggtgc cggcagcgct cttccgcttc   3120
ctcgctcact gactcgctgc gctcggtcgt tcggctgcgg cgagcggtat cagctcactc   3180
aaaggcggta atacggttat ccacagaatc aggggataac gcaggaaaga acatgtgagc   3240
aaaaggccag caaaaggcca ggaaccgtaa aaaggccgcg ttgctggcgt ttttccatag   3300
gctccgcccc cctgacgagc atcacaaaaa tcgacgctca agtcagaggt ggcgaaaccc   3360
gacaggacta taaagatacc aggcgtttcc ccctggaagc tccctcgtgc gctctcctgt   3420
tccgaccctg ccgcttaccg gatacctgtc cgcctttctc ccttcgggaa gcgtggcgct   3480
ttctcatagc tcacgctgta ggtatctcag ttcggtgtag gtcgttcgct ccaagctggg   3540
ctgtgtgcac gaaccccccg ttcagcccga ccgctgcgcc ttatccggta actatcgtct   3600
tgagtccaac ccggtaagac acgacttatc gccactggca gcagccactg gtaacaggat   3660
tagcagagcg aggtatgtag gcggtgctac agagttcttg aagtggtggc ctaactacgg   3720
ctacactaga agaacagtat ttggtatctg cgctctgctg aagccagtta ccttcggaaa   3780
aagagttggt agctcttgat ccggcaaaca aaccaccgct ggtagcggtg gtttttttgt   3840
ttgcaagcag cagattacgc gcagaaaaaa aggatctcaa gaagatcctt tgatcttttc   3900
tacggggtct gacgctcagt ggaacgaaaa ctcacgttaa gggattttgg tcatgagatt   3960
atcaaaaagg atcttcacct agatcctttt aaattaaaaa tgaagtttta atcaatctaa   4020 agtatatat gagtaaactt ggtctgacag ttaccaatgc ttaatcagtg aggcacctat   4080
ctcagcgatc tgtctatttc gttcatccat agttgcctga ctccccgtcg tgtagataac   4140
tacgatacgg gagggcttac catctggccc cagtgctgca atgataccgc gagacccacg   4200
ctcaccggct ccagatttat cagcaataaa ccagccagcc ggaagggccg agcgcagaag   4260
tggtcctgca actttatccg cctccatcca gtctattaat tgttgccggg aagctagagt   4320
aagtagttcg ccagttaata gtttgcgcaa cgttgttgcc attgctacag gcatcgtggt   4380
gtcacgctcg tcgtttggta tggcttcatt cagctccggt tcccaacgat caaggcgagt   4440
tacatgatcc cccatgttgt gcaaaaaagc ggttagctcc ttcggtcctc cgatcgttgt   4500
cagaagtaag ttggccgcag tgttatcact catggttatg gcagcactgc ataattctct   4560
tactgtcatg ccatccgtaa gatgcttttc tgtgactggt gagtactcaa ccaagtcatt   4620
```

```
ctgagaatag tgtatgcggc gaccgagttg ctcttgcccg gcgtcaatac gggataatac      4680
cgcgccacat agcagaactt taaaagtgct catcattgga aaacgttctt cggggcgaaa      4740
actctcaagg atcttaccgc tgttgagatc cagttcgatg taacccactc gtgcacccaa      4800
ctgatcttca gcatctttta ctttcaccag cgtttctggg tgagcaaaaa caggaaggca      4860
aaatgccgca aaaaagggaa taagggcgac acggaaatgt tgaatactca tactcttcct      4920
ttttcaatat tattgaagca tttatcaggg ttattgtctc atgagcggat acatatttga      4980
atgtatttag aaaaataaac aaataggggt tccgcgcaca tttccccgaa aagtgccacc      5040
tgacgcgccc tgtagcggcg cattaagcgc ggcgggtgtg gtggttacgc gcagcgtgac      5100
cgctacactt gccagcgccc tagcgcccgc tcctttcgct ttcttccctt cctttctcgc      5160
cacgttcgcc ggctttcccc gtcaagctct aaatcggggg ctccctttag ggttccgatt      5220
tagtgcttta cggcacctcg accccaaaaa acttgattag ggtgatggtt cacgtagtgg      5280
gccatcgccc tgatagacgg ttttcgccc tttgacgttg gagtccacgt tctttaatag      5340
tggactcttg ttccaaactg gaacaacact caaccctatc tcggtctatt cttttgattt      5400
ataagggatt ttgccgattt cggcctattg gttaaaaaat gagctgattt aacaaaaatt      5460
taacgcgaat tttaacaaaa tattaacgct tacaatttgc cattcgccat tcaggctgcg      5520
caactgttgg gaagggcgat cggtgcgggc ctcttcgcta ttacgccagc caagctacc       5580 atgataagta agtaatatta aggtacgtgg aggttttact tgcttttaaaa aacctcccac     5640 acctccccct gaacctgaaa cataaaatga atgcaattgt tgttgttaac ttgtttattg      5700
cagcttataa tggttacaaa taaagcaata gcatcacaaa tttcacaaat aaagcatttt      5760
tttcactgca ttctagttgt ggtttgtcca aactcatcaa tgtatcttat ggtactgtaa      5820
ctgagctaac ataa                                                        5834
```

<210> SEQ ID NO 5
<211> LENGTH: 5864
<212> TYPE: DNA
<213> ORGANISM: Artificial
<220> FEATURE:
<223> OTHER INFORMATION: synthetic

<400> SEQUENCE: 5

```
cccgggaggt accgagctct tacgcgtgct agctcgagtc tggggacttt ccgctgggga        60 cttttccgctg gggactttcc gctgggact tccgctggg gacttccgc agatctgcat        120 ctcaattagt cagcaaccat agtcccgccc ctaactccgc ccatcccgcc cctaactccg       180
cccagttccg cccattctcc gccccatggc tgactaattt ttttatttta tgcagaggcc       240
gaggccgcct cggcctctga gctattccag aagtagtgag gaggcttttt tggaggccta       300
ggcttttgca aaaagcttgg cattccggta ctgttggtaa atggaagac gccaaaaaca       360 taaagaaagg cccggcgcca ttctatcctc tagaggatgg aaccgctgga gagcaactgc       420
ataaggctat gaagagatac gccctggttc ctggaacaat tgcttttaca gatgcacata       480
tcgaggtgaa catcacgtac gcggaatact tcgaaatgtc cgttcggttg gcagaagcta       540
tgaaacgata tgggctgaat acaaatcaca gaatcgtcgt atgcagtgaa aactctcttc       600
aattctttat gccggtgttg ggcgcgttat ttatcggagt tgcagttgcg cccgcgaacg       660
acatttataa tgaacgtgaa ttgctcaaca gtatgaacat ttcgcagcct accgtagtgt       720
ttgtttccaa aaagggggttg caaaaaattt tgaacgtgca aaaaaaatta ccaataatcc       780
agaaaattat tatcatggat tctaaaacgg attaccaggg atttcagtcg atgtacacgt       840
```

```
tcgtcacatc tcatctacct cccggtttta atgaatacga ttttgtacca gagtcctttg      900
atcgtgacaa aacaattgca ctgataatga attcctctgg atctactggg ttacctaagg      960
gtgtggccct tccgcataga actgcctgcg tcagattctc gcatgccaga gatcctattt     1020
ttggcaatca aatcattccg gatactgcga ttttaagtgt tgttccattc catcacggtt     1080
ttggaatgtt tactacactc ggatatttga tatgtggatt tcgagtcgtc ttaatgtata     1140
gatttgaaga agagctgttt ttacgatccc ttcaggatta caaaattcaa agtgcgttgc     1200
tagtaccaac cctatttca ttcttcgcca aaagcactct gattgacaaa tacgatttat      1260
ctaatttaca cgaaattgct tctgggggcg cacctctttc gaaagaagtc ggggaagcgg     1320
ttgcaaaacg cttccatctt ccagggatac gacaaggata tgggctcact gagactacat     1380
cagctattct gattacaccc gaggggatg ataaaccggg cgcggtcggt aaagttgttc      1440
cattttttga agcgaaggtt gtggatctgg ataccgggaa aacgctgggc gttaatcaga     1500
gaggcgaatt atgtgtcaga ggacctatga ttatgtccgg ttatgtaaac aatccggaag     1560
cgaccaacgc cttgattgac aaggatggat ggctacattc tggagacata gcttactggg     1620
acgaagacga acacttcttc atagttgacc gcttgaagtc tttaattaaa tacaaaggat     1680
atcaggtggc ccccgctgaa ttggaatcga tattgttaca acaccccaac atcttcgacg     1740
cgggcgtggc aggtcttccc gacgatgacg ccggtgaact tcccgccgcc gttgttgttt     1800
tggagcacgg aaagacgatg acggaaaaag agatcgtgga ttacgtcgcc agtcaagtaa     1860
caaccgcgaa aaagttgcgc ggaggagttg tgtttgtgga cgaagtaccg aaaggtctta     1920
ccggaaaact cgacgcaaga aaaatcagag agatcctcat aaaggccaag aagggcggaa     1980
agtccaaatt gtaaaatgta actgtattca gcgatgacga aattcttagc tattgtaata     2040
ctgcgatgag tggcagggcg gggcgtaatt ttttaaggc agttattggt gcccttaaac      2100
gcctggttgc tacgcctgaa taagtgataa taagcggatg aatggcagaa attcgccgga     2160
tctttgtgaa ggaaccttac ttctgtggtg tgacataatt ggacaaacta cctacagaga     2220
tttaaagctc taaggtaaat ataaaattt taagtgtata atgtgttaaa ctactgattc      2280
taattgtttg tgtattttag attccaacct atggaactga tgaatgggag cagtggtgga     2340
atgcctttaa tgaggaaaac ctgttttgct cagaagaaat gccatctagt gatgatgagg     2400
ctactgctga ctctcaacat tctactcctc caaaaaagaa gagaaaggta gaagacccca     2460
aggactttcc ttcagaattg ctaagttttt tgagtcatgc tgtgtttagt aatagaactc     2520
ttgcttgctt tgctatttac accacaaagg aaaaagctgc actgctatac aagaaaatta     2580
tggaaaaata ttctgtaacc tttataagta ggcataacag ttataatcat aacatactgt     2640
tttttcttac tccacacagg catagagtgt ctgctattaa taactatgct caaaaattgt     2700
gtacctttag cttttaatt tgtaagggg ttaataagga atatttgatg tatagtgcct       2760
tgactagaga tcataatcag ccataccaca tttgtagagg ttttacttgc tttaaaaaac     2820
ctcccacacc tccccctgaa cctgaaacat aaaatgaatg caattgttgt tgttaacttg     2880
tttattgcag cttataatgg ttacaaataa agcaatagca tcacaaattt cacaaataaa     2940 gcatttttt cactgcattc tagttgtggt ttgtccaaac tcatcaatgt atcttatgat      3000
gtctggatcc gtcgaccgat gcccttgaga gccttcaacc cagtcagctc cttccggtgg     3060
gcgcggggca tgactatcgt cgccgcactt atgactgtct tctttatcat gcaactcgta     3120
ggacaggtgc cggcagcgct cttccgcttc ctcgctcact gactcgctgc gctcggtcgt     3180
tcggctgcgg cgagcggtat cagctcactc aaaggcggta atacggttat ccacagaatc     3240
```

```
agggatanc gcaggaaaga acatgtgagc aaaaggccag caaaaggcca ggaaccgtaa      3300
aaaggccgcg ttgctggcgt ttttccatag gctccgcccc cctgacgagc atcacaaaaa      3360
tcgacgctca agtcagaggt ggcgaaaccc gacaggacta taaagatacc aggcgtttcc      3420
ccctggaagc tccctcgtgc gctctcctgt tccgaccctg ccgcttaccg gatacctgtc      3480
cgcctttctc ccttcgggaa gcgtggcgct ttctcatagc tcacgctgta ggtatctcag      3540
ttcggtgtag gtcgttcgct ccaagctggg ctgtgtgcac gaaccccccg ttcagcccga      3600
ccgctgcgcc ttatccggta actatcgtct tgagtccaac ccggtaagac acgacttatc      3660
gccactggca gcagccactg gtaacaggat tagcagagcg aggtatgtag gcggtgctac      3720
agagttcttg aagtggtggc ctaactacgg ctacactaga agaacagtat ttggtatctg      3780
cgctctgctg aagccagtta ccttcggaaa aagagttggt agctcttgat ccggcaaaca      3840
aaccaccgct ggtagcggtg gttttttgt ttgcaagcag cagattacgc gcagaaaaaa      3900
aggatctcaa gaagatcctt tgatcttttc tacgggtct gacgctcagt ggaacgaaaa      3960
ctcacgttaa gggattttgg tcatgagatt atcaaaaagg atcttcacct agatcctttt      4020
aaattaaaaa tgaagtttta aatcaatcta agtatatat gagtaaactt ggtctgacag      4080
ttaccaatgc ttaatcagtg aggcacctat ctcagcgatc tgtctatttc gttcatccat      4140
agttgcctga ctccccgtcg tgtagataac tacgatacgg gagggcttac catctggccc      4200
cagtgctgca atgataccgc gagacccacg ctcaccggct ccagatttat cagcaataaa      4260
ccagccagcc ggaagggccg agcgcagaag tggtcctgca actttatccg cctccatcca      4320
gtctattaat tgttgccggg aagctagagt aagtagttcg ccagttaata gtttgcgcaa      4380
cgttgttgcc attgctacag gcatcgtggt gtcacgctcg tcgtttggta tggcttcatt      4440
cagctccggt tcccaacgat caaggcgagt tacatgatcc cccatgttgt gcaaaaaagc      4500
ggttagctcc ttcggtcctc cgatcgttgt cagaagtaag ttggccgcag tgttatcact      4560
catggttatg gcagcactgc ataattctct tactgtcatg ccatccgtaa gatgcttttc      4620
tgtgactggt gagtactcaa ccaagtcatt ctgagaatag tgtatgcggc gaccgagttg      4680
ctcttgcccg gcgtcaatac gggataatac cgcgccacat agcagaactt taaaagtgct      4740
catcattgga aaacgttctt cggggcgaaa actctcaagg atcttaccgc tgttgagatc      4800
cagttcgatg taacccactc gtgcacccaa ctgatcttca gcatctttta ctttcaccag      4860
cgtttctggg tgagcaaaaa caggaaggca aaatgccgca aaaaagggaa taagggcgac      4920
acggaaatgt tgaatactca tactcttcct ttttcaatat tattgaagca tttatcaggg      4980
ttattgtctc atgagcggat acatatttga atgtatttag aaaaataaac aaataggggt      5040
tccgcgcaca tttccccgaa aagtgccacc tgacgcgccc tgtagcggcg cattaagcgc      5100
ggcgggtgtg gtggttacgc gcagcgtgac cgctacactt gccagcgccc tagcgcccgc      5160
tcctttcgct ttcttccctt cctttctcgc cacgttcgcc ggctttcccc gtcaagctct      5220
aaatcggggg ctccctttag ggttccgatt tagtgcttta cggcacctcg accccaaaaa      5280
acttgattag ggtgatggtt cacgtagtgg gccatcgccc tgatagacgg ttttcgccc       5340
tttgacgttg gagtccacgt tctttaatag tggactcttg ttccaaactg gaacaacact      5400
caaccctatc tcggtctatt cttttgattt ataagggatt ttgccgattt cggcctattg      5460
gttaaaaaat gagctgattt aacaaaaatt taacgcgaat tttaacaaaa tattaacgct      5520
tacaatttgc cattcgccat tcaggctgcg caactgttgg gaagggcgat cggtgcgggc      5580
ctcttcgcta ttacgccagc ccaagctacc atgataagta agtaatatta aggtacgtgg      5640
```

```
aggttttact tgctttaaaa aacctcccac acctccccct gaacctgaaa cataaaatga    5700
atgcaattgt tgttgttaac ttgtttattg cagcttataa tggttacaaa taaagcaata    5760
gcatcacaaa tttcacaaat aaagcatttt tttcactgca ttctagttgt ggtttgtcca    5820
aactcatcaa tgtatcttat ggtactgtaa ctgagctaac ataa                      5864
```